(12) United States Patent
Bassett et al.

(10) Patent No.: US 12,343,454 B2
(45) Date of Patent: Jul. 1, 2025

(54) HYDROGELS FORMED IN SITU AND COMPOSITION DESIGN FOR INTRAUTERINE USE

(71) Applicant: Pramand LLC, Bedford, MA (US)

(72) Inventors: Michael Bassett, Hampton, NH (US); Ian Feldberg, Sudbury, MA (US)

(73) Assignee: Pramand LLC, Bedford, MA (US)

( * ) Notice: Subject to any disclaimer, the term of this patent is extended or adjusted under 35 U.S.C. 154(b) by 746 days.

(21) Appl. No.: 17/522,727

(22) Filed: Nov. 9, 2021

(65) Prior Publication Data

US 2022/0143276 A1 May 12, 2022

Related U.S. Application Data

(63) Continuation-in-part of application No. 17/494,752, filed on Oct. 5, 2021.

(60) Provisional application No. 63/113,013, filed on Nov. 12, 2020.

(51) Int. Cl.
*A61L 31/14* (2006.01)
*A61L 31/04* (2006.01)
*A61L 31/18* (2006.01)

(52) U.S. Cl.
CPC ............ *A61L 31/145* (2013.01); *A61L 31/041* (2013.01); *A61L 31/18* (2013.01); *A61L 2300/424* (2013.01); *A61L 2300/802* (2013.01)

(58) Field of Classification Search
CPC ...... A61L 31/145; A61L 31/041; A61L 31/18; A61L 2300/424; A61L 2300/802
See application file for complete search history.

(56) References Cited

U.S. PATENT DOCUMENTS

| | | | |
|---|---|---|---|
| 4,089,337 A | 5/1978 | Kronner | |
| 4,538,920 A | 9/1985 | Drake | |
| 4,741,872 A | 5/1988 | De Luca et al. | |
| 4,775,362 A | 10/1988 | Kronner | |

(Continued)

FOREIGN PATENT DOCUMENTS

GB      23 056 09      4/1997

OTHER PUBLICATIONS

Yi et al., "Pharmacokinetic properties and antitumor efficacy of the 5-fluorouracil loaded PEG-hydrogel," in BMC Cancer 2010, 10: 211, pp. 1-8. (Year: 2010).*

(Continued)

*Primary Examiner* — Blessing M Fubara
(74) *Attorney, Agent, or Firm* — Christensen, Fonder, Dardi PLLC; Diane E. Bennett; Peter S. Dardi

(57) ABSTRACT

Medical hydrogel systems for providing improved properties for certain medical applications are described. The hydrogel systems are effective for forming a space filling hydrogel in a body cavity and for the prevention of adhesion formation between tissues within the body cavity following a surgical procedure. Hydrogel delivery systems for transcervical delivery of a premixed precursor solution and an accelerator solution are described. Methods for transcervical installation of intrauterine hydrogels with distended fill are also described. The hydrogel systems, hydrogel delivery systems, and associated methods can be useful for providing degradable hydrogel in the uterine cavity, including the cervical canal, for the prevention of adhesions following intrauterine procedures.

36 Claims, 14 Drawing Sheets

(56) References Cited

U.S. PATENT DOCUMENTS

| | | | |
|---|---|---|---|
| 4,826,945 | A | 5/1989 | Cohn et al. |
| 4,938,763 | A | 7/1990 | Dunn et al. |
| 5,100,992 | A | 3/1992 | Cohn et al. |
| 5,160,745 | A | 11/1992 | De Luca et al. |
| 5,410,016 | A | 4/1995 | Hubbell et al. |
| 6,602,243 | B2 | 8/2003 | Noda |
| 6,706,026 | B1 | 3/2004 | Goldstein et al. |
| 7,009,034 | B2 | 3/2006 | Pathak et al. |
| 7,332,566 | B2 | 2/2008 | Pathak et al. |
| 7,347,850 | B2 | 3/2008 | Sawhney |
| 7,790,141 | B2 | 9/2010 | Pathak et al. |
| 8,003,705 | B2 | 8/2011 | Sawhney et al. |
| 8,210,453 | B2 | 7/2012 | Hull et al. |
| 8,383,161 | B2 | 2/2013 | Campbell et al. |
| 8,409,606 | B2 | 4/2013 | Sawhney et al. |
| 8,616,468 | B2 | 12/2013 | Hull et al. |
| 8,647,670 | B2 | 2/2014 | Shu |
| 9,125,807 | B2 | 9/2015 | Sawhney et al. |
| 9,492,383 | B2 | 11/2016 | Gravett et al. |
| 10,617,563 | B2 | 4/2020 | Jarrett et al. |
| 2001/0046518 | A1 | 11/2001 | Sawhney et al. |
| 2003/0012734 | A1 | 1/2003 | Pathak et al. |
| 2005/0266086 | A1 | 12/2005 | Sawhney |
| 2006/0147409 | A1* | 7/2006 | Pathak .................. A61K 9/0019 424/78.01 |
| 2008/0045924 | A1 | 2/2008 | Cox et al. |
| 2008/0187568 | A1* | 8/2008 | Sawhney ............. A61K 31/337 514/772.3 |
| 2009/0324721 | A1 | 12/2009 | Kennedy et al. |
| 2012/0035471 | A1 | 2/2012 | Lee-Sepsick et al. |
| 2014/0194733 | A1* | 7/2014 | Goforth .................... C07F 9/94 29/428 |
| 2016/0166504 | A1 | 6/2016 | Jarrett et al. |
| 2017/0354436 | A1 | 12/2017 | Holbrooks et al. |
| 2018/0008536 | A1 | 1/2018 | Jukarainen et al. |

OTHER PUBLICATIONS

Abbott J. et al., "SprayGel following surgery for Asherman's syndrome may improve pregnancy outcome", J Obstet Gynaecol. Sep. 2004;24(6):710-711. doi: 10.1080/01443610400008206.

Acunzo et al., "Effectiveness of auto-cross-linked hyaluronic acid gel in the prevention of intrauterine adhesions after hysteroscopic adhesiolysis: A prospective, randomized, controlled study" Human Reproduction, 18(9), 1918-1921 (2003).

Dizerega, "Use of Adhesion Prevention Barriers in Ovarian Surgery, Tubalplasty, Ectopic Pregnancy, Endometriosis, Adhesiolysis, and Myomectomy" Curr. Opin. Obstet. Gynechol. 8:3, 230-237 (1996).

Ge et al., "Recent Advances in Tissue Adhesives for Clinical Medicine", Polymers (2020), 12, 939; 22 pages.

Guida et al., "Effectiveness of auto-crosslinked hyaluronic acid gel in the prevention of intrauterine adhesions after hysteroscopic surgery: A prospective, randomized, controlled study" Human Reproduction, 19(6), 1461-1464 (2004).

Johns et al., "Initial feasibility study of a sprayable hydrogel adhesion barrier system in patients undergoing laparoscopic ovarian surgery" Fertility and Sterility, Abstract, 2 pages (Feb. 26, 2002).

Medley, John M. "Targeted Polymeric Biomaterials for the Prevention of Post Surgical Adhesions", University of Kentucky Doctoral Dissertations, 212 pages (2010).

Mettler et al., "New Adhesion Prevention Concept in Gynelogical Surgery", Scientific Paper JSLS(2003) 7:207-209.

Mettler et al., "Prospective Clinical Trial of SprayGel as a Barrier to Adhesion Formation: An Interim Analysis," Journal of the American Association of Gynecological Laparoscopists, vol. 10 No. 3, 339-344 (Aug. 2003).

Piredda et al., "Initial Feasibility Study of an Hydrogel Adhesion Barrier System in Patients Treated by Operative Hysteroscopy for Intrauterine Benign Pathologies" Supplement: The Journal of the American Association of Gynecologic Laparoscopists, vol. 10, No. 3, Abstract, 2 pages (Aug. 2003).

Torres-De La Roche et al., "Adhesions and Anti-Adhesion Systems Highlights" Facts Views Vis Obgyn, 11 (1):137-149 (2019).

Victory et al., "Risk of Endometrial and Ovarian Cancer in Patients with a History of Endometriosis-Related Infertility", The Journal of American Association of Gynecologic Laparoscopists, vol. 11, No. 3 Supplement, Abstract, 2 pages (Aug. 2004).

Wiseman, David M. "SprayShield: Approval status, clinical trials, reasons for delay, patient posts", International Adhesions Study www.adhesions.org/WisemanSprayshieldUpdate052412.pdf (2012).

International Search Report & Written Opinion from corresponding PCT application No. PCT/US2021/058957, dated Feb. 3, 2022, 11 pages.

European Search Report from corresponding European patent application No. 21892797.8, dated Sep. 30, 2024, 8 pages.

* cited by examiner

HYDROGELS FORMED IN SITU AND COMPOSITION DESIGN FOR INTRAUTERINE USE

CROSS REFERENCE TO RELATED APPLICATIONS

This application is a continuation in part application of U.S. patent application Ser. No. 17/494,752 filed on Oct. 5, 2021 to Bassett et al., entitled "Placement of Hydrogels Formed In Situ, Composition Design and Delivery Tools for Intrauterine Use," and claims priority to U.S. provisional patent application Ser. No. 63/113,013 filed on Nov. 12, 2020 to Bassett et al., entitled "Transcervical Access Systems for Intrauterine Fluid Exchange, Such as Placement of Hydrogels Formed In Situ", both of which are incorporated herein by reference.

FIELD OF USE

Aspects of the invention relate to hydrogels designed for transcervical delivery to the uterine cavity, including hydrogels useful for the placement using improved instrumentation, and delivery of these materials.

BACKGROUND

The unwanted adherence of scar tissue following medical intervention is a common complication termed adhesions. The formation of adhesions typically occurs when two injured tissue surfaces are close to one another. This complication can lead to painful and debilitating medical problems, including but not limited to postoperative adverse events and failure of the medical intervention. Adhesions that occur within the uterine cavity following transcervical procedures can often cause infertility. Surgical dissection of adhesions, a procedure known as adhesiolysis, can result in secondary adhesion re-formation. Current methods for preventing the formation of post-surgical adhesions, including but not limited to, intrauterine adhesions, have limited effectiveness.

SUMMARY OF THE INVENTION

Hydrogel systems are presented that provide for improved properties for certain medical applications, in particular adhesion prevention. The resulting hydrogels are biodegradable, and form into a hydrogel within seconds of delivery. The hydrogels are biocompatible and soft, yet the hydrogels have appropriate elastic modulus to remain in place against bodily forces for a desired period of time. The hydrogel precursors are resistant to dilution effects by ambient fluids following delivery to form a space filling hydrogel. The hydrogel systems involve mixing two precursors, an electrolyte and a nucleophile prior to delivery at a pH that limits premature crosslinking. The mixed precursors are blended with a basic buffer in an accelerator solution at delivery to drive the gelation.

The hydrogel systems are useful for methods and applications for preventing adhesions, including but not limited to intrauterine adhesions, as presented herein. These technologies may also be used to stop unwanted bleeding post-surgery and to provide mechanical support for uterine tissues. Materials may be introduced into a surgical site to reduce or prevent contact between damaged tissues, or portions of the tissues. Flowable components may be used so as to ease the introduction and formation of the materials. For example, flowable polymer precursors may be introduced in a laparoscopic or transcervical manner and activated to form a material on or in the uterus after its introduction. Examples of precursors include polymerizable/crosslinkable, hydrophilic polymers that form a material, e.g., a hydrogel, inside the uterine cavity.

Some embodiments relate to a method of preventing adhesion of damaged tissue surfaces in a potential space, such as uterine cavity. The method comprises introducing a flowable material into the uterine cavity to fill and tamponade the opposed cavity walls within the uterus. The tamponade can be effective to reduce bleeding from damaged tissues after surgical procedures and separating the damaged tissue surfaces to allow independent healing uterine cavity walls. By filling and distending the uterine cavity, the in-situ formed material will not be expelled by the muscular contractions of the uterus until loss of structural integrity occurs. The material may be, e.g., a hydrogel and may function as a stent or a splint. Some embodiments relate to a method of preventing intrauterine adhesions in a uterus by application of a material crosslinking precursors to form a hydrogel in the uterus, e.g., to coat the surface of damaged tissue, or tamponade a surface of the uterine cavity, or to prevent the collapse and adherence of the uterine cavity walls to each other. Some polymer systems involve the pre mixing of hydrogel precursors into one solution and the activation of the crosslinking during application by combining the precursor solution with a second solution for activation/acceleration. Applicator embodiments can relate to a design of the application device include the use of a soft, flexible atraumatic catheter, and a low catheter profile for reduction of remaining insertion track after removal. For transcervical access to the uterus, the applicator can comprise or be associated with a flow restrictor that helps to maintain the hydrogel precursor within the uterine cavity such that separation of the uterine walls is achieved by complete filling of the uterine cavity. In some embodiments, the flow restrictor can be adjusted along the catheter length, to position the catheter port at a specific location within the uterine cavity.

In one aspect, the invention pertains to a crosslinked hydrogel composition comprising multi-armed polyethylene glycol molecules crosslinked with a multifunctional crosslinker with biodegradable crosslinking bond. The hydrogel can have an in vivo, intrauterine degradation time from about 1 day to about 21 days. To provide stability without undesirable pressure on the patient for in vivo use, the hydrogel can have values of Young's modulus from 5 kPa to 300 kPa. In some embodiments, the crosslinking molecule incorporated into the hydrogel is a polyamine, such as polylysine, which can be trilysine. In some embodiments, the crosslinking functional groups are N-hydroxy succinimide esters and primary amines that react to form amide bonds through nucleophilic substitution.

In another aspect, the invention relates to a hydrogel applicator that comprises two reservoirs with outlets connected to a Y-connector to intermix the respective solutions from the reservoirs in a section of tubing that connects to a catheter having a size of no more than 9Fr having an outlet port on the side of the catheter body with an atraumatic tip. One reservoir can hold a blend of hydrogel precursors under conditions for the crosslinking to be sufficiently slow, and the other reservoir can then comprise an accelerant, such as a basic buffer. The reservoirs can be syringe tubes mounted in a holder the plungers connected to a plunger cap to prove for convenient simultaneous deployment of the two syringe plungers. A static mixer can provide more rapid mixing of the combined solutions from the reservoir. The catheter can be formed from a sufficiently low durometer value polymer so that it is less likely to cause injury to the patient's tissue.

In a first particular aspect, the invention pertains to a medical hydrogel system comprising a precursor blend solution and an accelerator solution. The precursor blend solution can comprise a aqueous solvent, a first precursor having a hydrophilic core and succinimidyl ester functional groups, and a second precursor having a plurality of amine functional groups, in which the precursor blend solution has an acid pH. The accelerator solution can comprise a buffer solution having a pH greater than 8.2 and a sufficient buffer capacity to raise the pH of a mixture of the precursor blend solution and the accelerator solution above a pH of 8.

In a further particular aspect, the invention pertains to a hydrogel delivery system suitable for intrauterine delivery comprising a first solution, a second solution and an applicator. The applicator can comprise a catheter configured for transcervical intrauterine placement with a cap element on the catheter to allow for stopping egress of hydrogel from the cervix, a first reservoir holding the first solution, a second reservoir holding the second solution, a mixer configured for receiving the first solution and the second solution and vigorously mixing the first solution and the second solution to form a blended precursor solution for delivery to the catheter from the mixer, the blended precursor solution having 5 weight percent (wt %) to 12 wt % solids. Generally, the blended precursor solution gels in no more than about 30 seconds and after 12 hours forms a product hydrogel with an initial Young's modulus greater than 1 kPa, and the product hydrogel persists in a uterine environment for 3 to 29 days.

In another particular aspect, the invention pertains to a method for delivering an intrauterine hydrogel, the method comprising combining a first solution and a second solution to form a blended solution, and directing the blended solution into a transcervical positioned catheter to deliver the blended solution into a uterus. Generally, the first solution comprises an aqueous solvent, a first precursor having a hydrophilic core and succinimidyl ester functional group, and a second precursor having a plurality of amine functional groups, and the second solution generally comprises a buffer solution having a pH greater than 8.2. The blended solution can undergo covalent crosslinking to gel in no more than 30 seconds, wherein the catheter has a cap element that can be used to prevent egress of the blended solution to provide pressure to the gelling hydrogel creating distended fill.

DETAILED DESCRIPTION OF THE INVENTION

Figure 1:
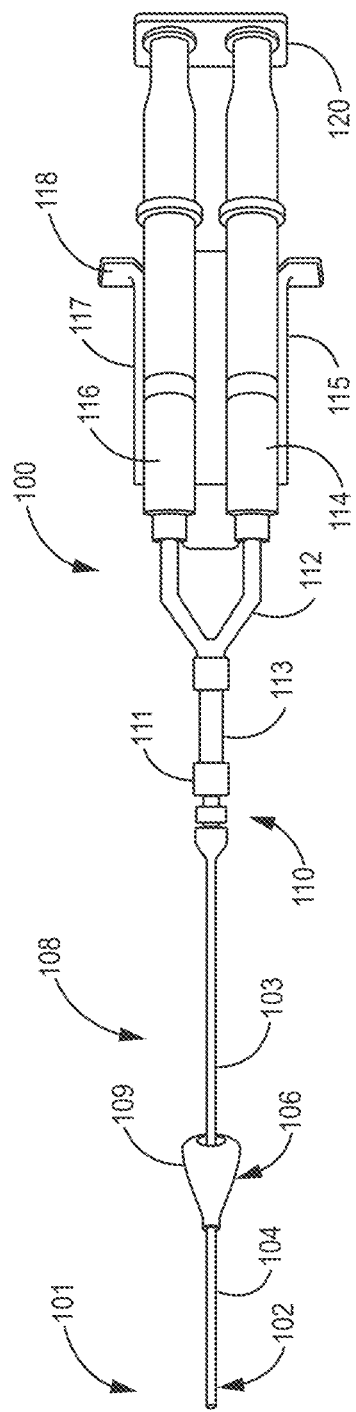
FIG. 1 is a depiction of an intrauterine applicator for transcervical delivery of a crosslinking hydrogel precursor solution.

Hydrogel formulations are discovered that provide for particular properties that are suitable for medical applications, in particular for intrauterine delivery, although the hydrogels can be suitable for other appropriate medical procedures. Delivery into the uterine cavity provides several significant challenges. With respect to delivery, the precursor solution in its initial gel state should flow well to fill the uterine cavity without flowing past the uterine ostium into the fallopian tubes or out through the cervix and should set as a gel quickly to achieve these countervailing objectives. The uterine cavity can exert forces to excrete materials out of the uterine cavity through the cervix, so the hydrogel should have sufficient resilience that it can be maintained within the uterus against these forces. The hydrogels are biodegradable and should persist long enough to prevent adhesions but not too long so as to contribute to problems themselves. While the challenges are significant, hydrogels are designed based on one precursor with hydrophilic cores, especially polyethylene glycol cores, with succinimidyl ester functional groups and a second precursor with a plurality of amine functional groups. To resist dilution effects, the hydrogel precursors are mixed prior to delivery, and combined with an accelerator solution during delivery to effectively fill the uterine cavity while providing desirable modulus and space filing properties. Effective applicators have been designed to allow for convenient delivery of the hydrogels. The resulting systems are well suited for effective medical procedures to alleviate risks from intrauterine adhesions or similar protected spaces in patients.

Based on the newly designed hydrogel systems, effective approaches are presented for reducing or eliminating intrauterine adhesions resulting from medical procedures through the delivery of appropriately designed hydrogel precursors using suitable applicators. Effective hydrogel precursors can be designed with respect to one or more of gelation times, viscosities of the precursor solutions, swelling degree after crosslinking, bio-degradation times, mechanical properties, or other appropriate features. Improvements with respect to these parameters can overcome shortcomings of earlier attempts to deliver useful products for adhesion prevention based on hydrogels. An improved applicator has been designed for more effective delivery into a cavity, such as a uterine space. The improved applicator can comprise an egress limiter that can inhibit outflow of hydrogel and/or hydrogel precursors out from the cervix prior to sufficient gelling of the precursors. A convenient design allows for the control of the flow limiter in a convenient procedure. The improved applicator is described below and additional features are described in copending U.S. patent application Ser. No. 17/494,752 to Bassett et al., entitled "Transcervical Access Systems for Intrauterine Fluid Exchange, Such as Hydrogels Formed In Situ," incorporated herein by reference.

In some embodiments, a mixture or a process of mixing hydrophilic reactive precursor species involves having nucleophilic functional groups with hydrophilic reactive precursor species and having electrophilic functional groups such that they form a mixture that crosslinks. If the mixture reacts relatively slowly under neutral conditions, the precursors can be mixed and placed into a syringe or comparable reservoir of the delivery system shortly before administration. An accelerant can be placed into the other syringe or comparable fluid reservoir. The accelerant can be mixed with the precursor blend during delivery to initiate more rapid crosslinking due to a pH change or other suitable property of the blend. Since the precursors can be well mixed prior to administration, the mixing process can be more complete in the delivery system such that well mixed compositions are delivered into the catheter for intrauterine delivery.

Certain embodiments of the invention are directed to methods and apparatus for delivering two solutions to form hydrogel implants in situ. As described herein, dual component hydrogel systems provide for effective use depositing such hydrogel systems into the intrauterine cavity, although the hydrogels can be effective for other confined spaces in a patient. The methods involve preparing the precursors in a suitable applicator with a catheter to receive mixed components of the hydrogel system. The catheter can interface with a flow limiter for delivering the hydrogel precursors into a confined space, such as the uterine cavity. The flow limiter can be left in place while the catheter is removed, and the flow limiter or portions thereof can be removed shortly thereafter with the precursors sufficiently gelled. With respect to terminology, hydrogel system refers to the two solutions used to form the hydrogel in appropriate containers. The transformation from hydrogel precursors to hydrogel is not a sharp conversion. So hydrogel precursors can appropriately be used to describe the separated components prior to initiation of crosslinking leading to gelling through sufficient gelling that the material no longer flows on its own, and hydrogel can refer to the materials following significant crosslinking leading to rheology changes to a fully set hydrogel following full crosslinking. Thus, there are transitory states that can reasonably be described with either term.

The use of hydrogels for intrauterine use was described in published U.S. patent application 2005/0266086 to Sawhney (hereinafter the '086 application), entitled "Intrauterine Applications of Materials Formed In Situ," incorporated herein by reference. A product called SprayGel™ was sold generally for prevention of adhesions. The '086 application specifically describes the use of SprayGel™ in its Examples. The product in SprayGel™ was covered under U.S. Pat. No. 7,009,034 to Pathak et al. (hereinafter the '034 patent), entitled "Biocompatible Crosslinked Polymers," incorporated herein by reference.

The hydrogel systems described herein overcome identified shortcoming of the previous products. In particular, the improved hydrogel systems have good flow to cover targeted space without uncontrolled movement of the hydrogel precursors beyond target areas. Also, the hydrogel systems are significantly less vulnerable to dilution effects. These improvements are particularly desirable for intrauterine delivery, such as for adhesion prevention, although the hydrogels are also useful for other medical applications, such as adhesion prevention in the abdominal cavity.

Adhesions (Intrauterine Adhesions)

Adhesions can form as part of a natural healing process and can connect adjacent injured tissues with clear fibrous bands. The adhesion barriers described herein, can be applicable to avoidance of any post-surgery adhesion formation, but the discussion focuses on intrauterine adhesions, for which the compositions are particularly well suited. Other adhesion prevention applications of note include delivery of the hydrogels for adhesion prevention in the abdominal cavity.

Intrauterine adhesions (IUAs) appear as adhesion bands with clear or irregular margins, which lead to distortions of natural uterine physiology, and ultimately may fill the uterine cavity (1). A partial or total blockage of the uterine cavity due to adhesions may result in abnormal bleeding, infertility, and recurrent pregnancy loss (2). For any of these reasons, avoidance of intrauterine adhesions is desirable. IUAs are commonly found in patients following gynecological procedures involving instrumentation placed in the uterus for either diagnostic or therapeutic purposes, or in patients having experienced trauma within the uterine cavity (3). The incidence of intrauterine adhesion formation following such events can be as high as 60% (4). Adhesions are the results of operative hysteroscopy, with rates varying with the type of procedure involved, and notably high rates in metroplasty, myomectomy, and endometrial ablations (5, 6). In these conditions while treating the primary cause of subfertility, one risks creating adhesions, which present a more insidious risk to fertility. The association between presence of adhesions and infertility has been reported as high as 43% (3). Furthermore, evidence suggests that the severity of adhesions may be progressive with mild, filmy adhesions that may advance to fibromuscular adhesions and ultimately developing into dense connective tissue (8). Various factors have been associated with intrauterine adhesions formation. (6, 9, 10, 11, 12).

The use of resorbable barriers for the prevention of IUAs has shown some clinical success in past years. Barriers include solutions of hyaluronic acid, crosslinked hyaluronic acid and viscoelastic solutions comprising hydrophilic polymers. Solutions of hyaluronic acid and crosslinked products such as Sepracoat (hyaluronic acid based product, Genzyme) were shown to be prophylactically effective but remain ineffective or lack data supporting the reduction of IUAs when applied after tissue injury has occurred (17). Viscoelastic forms have shown promising clinical results in the overall reduction of IUAs but remain subject to premature dilution and are challenged to stretch overall persistence times. To date, there is still no single modality proven to be satisfactorily effective in preventing post-operative adhesion formation for hysteroscopic use (18).

In-situ forming hydrogels offer several advantages in use as an adhesion barrier. The liquid nature of the precursors allows for ease-of-use, minimized invasiveness and thorough application to the entire uterine cavity. After formation of the gel through crosslinking, the barrier is more resistant to expulsion from the uterine cavity and to premature dilution. Hydrogel formulations are generally described that can achieve persistence times designed to the prevention of IUAs. Previous efforts for the application of hydrogels for the prevention of intrauterine adhesions is described in the '086 application, cited above. The Examples of the '086 application used a material referred to as SPRAYGEL, which was developed and demonstrated to be useful for prevention intraperitoneal adhesion formation (5,6,7), see Mettler et al., "Prospective Clinical Trial of SprayGel as a Barrier to Adhesion Formation: An Interim Analysis," Journal of the American Association of Gynecological Laparoscopists, (August 2003) 10 (3), 339-344, incorporated herein by reference. SPRAYGEL was comprised of two liquids (one clear and one blue) that each contain chemically distinct polymeric precursors which, when mixed together, rapidly cross-link to form a biocompatible absorbable hydrogel in situ. As noted above, additional details for the hydrogels under in SPRAYGEL are provided in the '034 patent. The evaluation of a hydrogel material for prevention of intrauterine adhesions were conducted using compositions and devices designed for intraperitoneal applications (19, 20). The intrauterine environment presents unique challenges of restricted space, contractions of the uterine muscle, and exit pathway out of the body, different healing mechanism after injury, potential dilution due to the presence of fluids in the cavity, and other differences, relative to the intraperitoneal environment. Thus, specific compositions are desirable to achieve target results for intrauterine adhesion prevention. Improved delivery devices for intrauterine applications are described in copending U.S. patent application Ser. No. 17/494,792 to Bassett et al. (hereinafter the '792 application), entitled "Transcervical Access Systems For Intrauterine Fluid Exchange, Such as Placement of Hydrogels Formed In Situ," incorporated herein by reference.

Hydro gels For Medical Applications

Hydrogels generally are considered materials that absorb water, undergo swelling without discernible dissolution, and maintain three-dimensional networks capable of reversible deformation. See, e.g., Park, et al., Biodegradable Hydrogels for Drug Delivery, Technomic Pub. Co., Lancaster, PA (1993), incorporated herein by reference. Covalently cross-linked networks of hydrophilic polymers, including water-soluble polymers are traditionally denoted as hydrogels (or aquagels) in the hydrated state. Hydrogels have been prepared based on crosslinked polymeric chains of methoxy-poly(ethylene glycol) monomethacrylate having variable lengths of the polyoxyethylene side chains, and their interaction with blood components has been studied (Nagaoka et al., in Polymers as Biomaterial (Shalaby et al., Eds.) Plenum Press, 1983, p. 381).

Crosslinkable solutions for use include those that may be used to form implants in lumens or voids, and may form physical crosslinks, chemical crosslinks, or both. Physical crosslinks may result from complexation, hydrogen bonding, desolvation, Van der Waals interactions, ionic bonding, etc., and may be initiated by mixing two components that are physically separated until combined in situ, or as a consequence of a prevalent condition in the physiological environment, such as temperature, pH, ionic strength, etc. Chemical crosslinking may be accomplished by any of a number of mechanisms, including free radical polymerization, condensation polymerization, anionic or cationic polymerization, step growth polymerization, etc. Where two solutions are employed, each solution contains components of a co-initiating system that initiate crosslinking on mixing. The solutions are separately stored and mixed for delivery into a tissue lumen. The improved hydrogel systems described herein are based on two solutions that mix to chemically crosslink.

Hydrogels may be crosslink spontaneously from at least one precursor without requiring the use of a separate energy source. In the case of a dual-component system, mixing of the two solutions takes place so that the solutions are fluid while passing through the device. If desired, one or both crosslinkable precursor solutions may contain contrast agents or other means for visualizing the hydrogel implant. The crosslinkable solutions may contain a bioactive drug or other therapeutic compound that is entrapped in the resulting implant, so that the hydrogel implant serves a drug delivery function.

Properties of the hydrogel system, other than crosslinkability, can be selected according to the intended application. For example, if the hydrogel implant is to be used to temporarily fill and tamponade a reproductive organ, such as the uterine cavity, the hydrogel system can undergo some swelling to conform to irregular geometries and be biodegradable within the timeframe of a single menstrual cycle. The hydrogel is preferably soft and of a modulus or stiffness that is lower than that of uterine tissue in a non-gravid uterus. Other applications may suggest different characteristics of the hydrogel system. More generally for medical applications, the materials should be selected on the basis of exhibited biocompatibility and lack of toxicity.

A hydrogel may be biodegradable, so that it does not have to be retrieved from the body. Biodegradability, as used herein, refers to the predictable disintegration of the material into molecules or particles small enough to be metabolized or excreted under normal physiological conditions. Biodegradability may occur by, e.g., hydrolysis, enzymatic action, cell-mediated destruction, combinations thereof, or the like.

Hydrogel Systems with Chemical Crosslinking

The hydrogel systems described herein to provide desirable space filling medical functions, especially for reducing adhesions, are provided in two solutions that are generally combined during delivery into the patient. The hydrogel precursors can be designed to spontaneously crosslink in the mixed solution based on a nucleophilic-electrophilic reaction. Through the appropriate design of the hydrogel systems, the precursors can be designed so that the precursors are combined into one solution that is stable against crosslinking and a second solution comprises an initiator that initiates the crosslinking reaction following mixing.

Thus, a first aspect of the design of the polymer system is the formation of an appropriately stable initial blend of the precursors. While the polymer precursors should be appropriately stable to not significantly crosslink prior to delivery, the blended solutions should result in rapid crosslinking. Due to these combinations of features, the configuration of the solutions for delivery can result in a hydrogel with slightly different properties relative to hydrogels formed with a different initial configuration in the solutions. The biodegradation rates is influenced by the incorporation of biodegradable linkages in the hydrogel. The basic chemical structures of the hydrogels and there precursors are described next in the context of these general properties, and the hydrogel properties are described in more detail below.

The precursors generally comprise at least two different polymerizable compounds. To form highly crosslinked hydrogels, both precursors generally each have more than two reactive functional groups for forming crosslinks. In some embodiments, at least one of the precursor compounds us generally of moderate molecular weight and may be a polymer. Water soluble polymerizable polymeric monomers having a functionality>1 (i.e., that form crosslinked networks on polymerization) and that form hydrogels may be referred to herein as macromers. A second precursor compound can be a moderate molecular weight compound or a small molecule crosslinking agent. Molecular weight ranges are discussed further below. The functional groups of the precursors provide for the crosslinking reactions, the biodegradable feature as well as the overall properties of the precursor solutions and the product hydrogel.

Where two solutions are employed, each solution has generally contained one component of the polymerizing system that crosslink on contact. The solutions were stored in separate compartments of a delivery system, and mixed either when deposited on or within the tissue. In contrast, the polymer systems here are sufficiently stable that the two monomers are mixed in the delivery system prior to delivery and are combined with an initiating solution upon delivery, where at least one of the monomers is usually a macromer. Generally, pH is used to gate the crosslinking reaction. Thus, the initiating solution can lower the pH to allow for the crosslinking reactions to proceed, generally at a rapid rate.

If the crosslinking reactions proceed simultaneously with the mixing of the precursors, the morphology of the crosslinked hydrogel can be somewhat different. Also, the flow properties of the initiated crosslinking solutions can also be somewhat different without altering the gel times. So if mixing and crosslinking occur simultaneously, there is less homogeneity in the initial crosslinked material relative to a mixed precursor solution that is mixed with an initialization solution that primarily shifts the pH. The increased homogeneity improves the flow of the precursor solution leading up to the gel time where sufficient crosslinking effectively limits any further flow. After passing the gel time, further crosslinking occurs over an additional period of time.

In hydrogel systems, suitable functional groups for crosslinking macromers to form tissue implants in situ also may be advantageously used, including macromers that contain groups that demonstrate activity towards functional groups such as amines which may be present in the crosslinking compound. Thus, multi-component hydrogel systems can spontaneously crosslink when the components are activated by an initiating systems, but the two or more components are appropriately stable for a reasonable process time before activation. Such systems include, for example, contain monomers (macromers or small molecule) that are di or multifunctional amines in one component and macromers with di or multifunctional N-succinimidyl containing moieties in the other component. Succinimidyl functional groups facilitate amide bond formation in reactions with amines. Other initiator systems, such as components of redox type initiators, also may be used. The mixing of the two or more solutions may result in a condensation polymerization that further leads to the formation of an implant.

The solids concentration of the hydrogel precursor solution has been discovered to be significant for intrauterine delivery. The intrauterine space can contain various bodily fluid, and after medical procedures, blood and residual fluid from the procedure can also be present. While some fluid may be removed prior to instillation of the hydrogel into the intrauterine space, the hydrogel precursors can be diluted by the fluids in the space with the precursors are delivered. The dilution effect was problematic for the original SprayGel™ product, which was primarily designed for preventing intraabdominal adhesions. With dilution in the uterine cavity, the SprayGel™ hydrogel did not necessarily file the cavity and the modulus of the set hydrogel could be lower than target values. The improved hydrogels described herein are designed to be dilution resistant.

Hydrogel and precursor solution properties are described in detail below. Significant properties include: gel time, lack of clogging of applicator, low dilution effects/good spread through the cavity without excessive migration, appropriate biodegradation times, and maintenance of sufficient modulus for a desired period of time. Due to muscular function, the uterus tends to expel material from the cavity, so a modulus below certain values tend to be subject to expulsion from the uterine cavity. The parameters that influence these issues include: functional group chemistry, crosslinking density/molecular weights of the monomers, monomer composition, percent solids in the hydrogel precursors, buffer chemistry and ionic strength, Through the use of premixed precursors with acidified amine groups, the autohydrolysis of the product hydrogel is observed. Autohydrolysis can result in degradation of the hydrogel without effects of biological activity. Autohydrolysis can take place in the initially formed hydrogel prior to full removal of the buffer from the hydrogel through osmosis and exchange with bodily fluids. Autohydrolysis can result in premature decrease in the modulus of the hydrogel.

Monomers

Monomers capable of being crosslinked to form a biocompatible implant may be used. As noted above, monomers can be macromers or small molecule crosslinking agents and in either case may or may not be polymers. The term polymer, as used herein, means a molecule formed of at least three repeating groups. The term "reactive precursor species" means a polymer, functional polymer, macromolecule, small molecule, or small molecule crosslinker that can take part in a reaction to form a network of crosslinked molecules, e.g., a hydrogel.

Monomers may include the biodegradable, water-soluble macromers described in U.S. Pat. No. 7,332,566 to Pathak et al. (hereinafter the '566 patent), entitled "Biocompatible Crosslinked Polymers With Visualization Agents," incorporated herein by reference. These monomers are characterized by having at least two polymerizable groups, separated by at least one degradable region. When polymerized in water, they form coherent gels that persist until eliminated by bio-degradation. Generally, the macromer is formed with a core of a polymer that is water soluble and biocompatible, such as a polyalkylene oxide, e.g. polyethylene glycol, which can be flanked by hydroxy-carboxylic acids such as lactic acid. Suitable monomers, in addition to being biodegradable, biocompatible, and non-toxic, also can be at least somewhat elastic after crosslinking or curing. Crosslinkable monomers with amine groups include, for example, polyethylenimine, which can have selectable degrees of branching and molecular weights.

The macromers generally have biologically inert and water soluble cores. When the core is a polymeric region that is water soluble, polymers that may be used include: polyethers, for example, polyalkylene oxides such as polyethylene glycol ("PEG"), polyethylene oxide ("PEO"), polyethylene oxide-co-polypropylene oxide ("PPO"), co-polyethylene oxide block or random copolymers, poloxamers, such as Pluronic® F-127; as well as polyvinyl alcohol ("PVA"); poly (vinyl pyrrolidinone) ("PVP"); poly (amino acids); polysaccharides, such as hyaluronic acid or cellulose and derivatives thereof; dextran and proteins such as albumin. Based on extensive experience in existing medical products, polyethers and more particularly poly(oxyalkylenes) or poly(ethylene glycol) or polyethylene glycol are especially suitable. It has been determined that hydrogels formed with macromers with longer distances between crosslinks are generally softer, more compliant, and more elastic. Thus, in the polymers of the '566 patent, increased length of the water-soluble segment, such as polyethylene glycol, tends to enhance elasticity. Molecular weights of hydrophilic macromer cores, such as polyethylene glycol macromer cores, for desirable applications can be from about 5,000 to about 500,000, in further embodiments from about 7500 to about 100,000, in some embodiments from about 10,000 to about 50,000, and in other embodiments in the range of about 15,000 to about 40,000. As used herein, molecular weights (mass) are in conventional units, which can be equivalently Daltons or as a molar mass-grams/mole (assuming natural isotopic presence in either case), and for polymers molecular weights are generally reported as averages if there is any distribution of molecular weights. A person of ordinary skill in the art will recognize that additional ranges within the explicit ranges above are contemplated and are in the present disclosure.

Generally, the monomer providing electrophilic functional groups is a macromer. The monomer providing the amine functional groups can be a macromer or a small molecule crosslinker. Macromers with amine functional groups can fall within the molecular weight ranges of the previous paragraph for the macromers with electrophilic functional groups. While somewhat arbitrary, small molecule crosslinkers are identified herein as having a molecular weight of no more than 4500 and can be considered macromers if the molecular weight is greater than 4500. Thus small molecular crosslinkers can have molecular weights generally from 100 to about 4500, in further embodiments, from about 200 to about 2500, and in additional embodiments form about 225 to about 1500. A person of ordinary skill in the art will recognize that additional ranges of crosslinker molecular weights within the explicit ranges above are contemplated and are within the present disclosure. When the core is small molecular in nature, any of a variety of hydrophilic functionalities can be used to make the precursor water soluble. For example, functional groups like hydroxyl, amine, sulfonate and carboxylate, which are water soluble, maybe used to make the precursor water soluble. In addition, N-hydroxysuccinimide ("NHS") ester of subaric acid is insoluble in water, but by adding a sulfonate group to the succinimide ring, the NHS ester of subaric acid may be made water soluble, without significantly affecting its reactivity towards amine groups.

Biodegradable Linkages

If it is desired that the biocompatible crosslinked polymer be biodegradable or absorbable, one or more precursors having biodegradable linkages present in between the functional groups may be used. The biodegradable linkage optionally also may serve as part of the water soluble core of one or more of the precursors. In the alternative, or in addition, the functional groups of the precursors may be chosen such that the product of the reaction between them results in a biodegradable linkage. For each approach, biodegradable linkages may be chosen such that the resulting biodegradable biocompatible crosslinked polymer will degrade or be absorbed in a desired period of time. Generally, biodegradable linkages are selected that degrade under physiological conditions into non-toxic products.

The biodegradable linkage may be chemically or enzymatically hydrolyzable or absorbable. Illustrative enzymatically hydrolyzable biodegradable linkages include peptidic linkages cleavable by metalloproteinases and collagenases. Additional illustrative biodegradable linkages can be functional groups on the core polymers and copolymers, such as hydroxy-carboxylic acids, orthocarbonates, anhydrides, lactones, (aminoacids, carbonates, phosphonates or combinations thereof. In exemplified embodiments, the biodegradable linkages are hydroxy-carboxylic acid moieties adjacent the electrophilic group used for crosslinking.

Functional Groups and Crosslinking Reactions

The crosslinking reactions generally are designed to occur in aqueous solution in vivo, encircled by physiological conditions, where the hydrogel reaction occurs in a transient local environment. Thus, the crosslinking reactions occur "in situ", meaning they occur at local sites such as on organs or tissues in a living animal or human body. Due to the in situ nature of the reaction, the crosslinking reactions can be designed not to release undesirable amounts of heat of polymerization. Crosslinking times for desirable procedures are described above. Certain functional groups, such as alcohols or carboxylic acids, do not normally react with other functional groups, such as amines, under physiologically acceptable pH (e.g., pH 7.2-11.0, 37° C.). However, such functional groups can be made more reactive by using an activating group such as N-hydroxysuccinimide or derivatives thereof. Several methods for activating such functional groups are known in the art. Suitable activating groups include carbonyldiimidazole, sulfonyl chloride, aryl halides, sulfosuccinimidyl esters, N-hydroxysuccinimidyl ester (NHS), succinimidyl ester, epoxide, aldehyde, maleimides, imidoesters and the like. The N-hydroxysuccinimide esters or N-hydroxysulfosuccinimide groups are desirable groups for crosslinking of proteins or amine functionalized polymers such as amino terminated polyethylene glycol ("APEG") since they have found acceptance in medical implants from long periods of use in approved products.

The other functional group used for the crosslinking generally is an amine. Amines are weak bases, and the pKa of the protonated amines are dependent on the molecule. The protonated amines are generally not suitable for nucleophilic substitution. Thus, the precursor solution can be at a suitable pH to maintain substantially protonated amines prior to combining with the initiating solution. This pH adjustment can maintain the precursor solutions from prematurely crosslinking. Suitable small molecule amine precursors include lysine molecules and oligomers thereof. Specific small molecule amines include, for example, lysine, dilysine, trilysine, tetralysine, pentalysine, and mixtures thereof. The lysine amines are generally protonated under physiological (close to neutral) pH values. The use of a small molecule crosslinker for one precursor can provide for a relatively low viscosity of the blended precursors prior to extensive crosslinking such that the blended hydrogel precursors can be delivered through a thin catheter while crosslinking initiates and the fluid conforms to the shape of the uterine cavity, but then relatively rapid crosslinking in the presence of the accelerator provides for stabilization of the hydrogel within the uterus in a reasonable period of time. As the precursor blend flows across the tissue, the hydrogel forming during the crosslinking process conforms to the shape of the small features of the tissue such as bumps, crevices and any deviation from surface smoothness, although perfect conformation is not necessary.

While the mixed precursors are reasonably stable, their stability times are not long in the sense of product distribution. Thus, aqueous solutions of NHS based crosslinkers and functional polymers can be made just before the crosslinking reaction due to reaction of NHS groups with water. For example, two separate vials of the electrophile and the nucleophile can be combined and placed into a syringe tube. The expression "pot life" can refer to the time from mixing. Longer "pot life" may be obtained by keeping these solutions at lower pH. Generally, the pre-mixed precursors can be kept as a pH from about 3.5 to about 6.5, in some embodiments from about 3.75 to about 6.3 and in further embodiments from about 4 to about 6.2 pH units. Generally, a longer pot life will correlate with lower pH values over these ranges. These solutions generally are buffered to maintain the solutions at the appropriate pH values until mixed with the accelerator solution. Suitable buffers include, for example, phosphate buffer and/or citrate buffer. Suitable buffers may include biological buffers, for example, as sold by Sigma Aldrich. The precursor solution can have a total buffer salt concentration from about 2 mM (millimolar) to about 500 mM, in further embodiments from about 5 mM to about 300 mM, in other embodiments from about 7 mM to about 150 mM, and in some embodiments from about 10 mM to about 100 mM. Adjustment of the pH can be accomplished with appropriate addition of a strong acid or base to get a target pH. With the reactants described herein, reasonable a pot life is readily achievable. Suitable pot lives can be at least about 5 minutes, in some embodiments at least about 10 minutes, and in other embodiments from about 12 minutes to about 10 hours. A person of ordinary skill in the art will recognize that additional ranges of pH, buffer concentrations and pot life times within the explicit ranges above are contemplated and are within the present disclosure.

The crosslinking density of the resultant biocompatible crosslinked polymer is controlled by the overall molecular weight of the crosslinker and functional polymer and the number of functional groups available per molecule. A lower molecular weight between crosslinks such as 600 Da will give much higher crosslinking density as compared to a higher molecular weight such as 10,000 Da. Higher molecular weight functional polymers can be used to obtain more elastic gels.

The crosslinking density also may be controlled by the overall percent solids of the crosslinker and functional polymer solutions. Increasing the percent solids increases the probability that an electrophilic functional group will combine with a nucleophilic functional group prior to inactivation by hydrolysis. Yet another method to control crosslink density is by adjusting the stoichiometry of nucleophilic functional groups to electrophilic functional groups. A one to one ratio leads to the highest crosslink density. In general, over time, the hydrogel completes curing so that available crosslinking sites form crosslinking bonds. If the electrophilic and nucleophilic are provided in equal equivalent amounts it can be expected that approximately all functional groups form crosslinking bonds after full curing. Equal numbers (or reaction equivalents) of the two types agents provides the highest crosslinking density. If a different ratio of functional groups is used, the properties of the cured hydrogel can be accordingly somewhat different. The crosslinking density can be depend on the number of functional groups on the precursor molecules as well as the ratio of precursor molecules. A non-stoichiometric ratio of electrophilic and nucleophilic groups can be used to alter the crosslinking density if desired. In some embodiments, the ratio of electrophilic functional groups to nucleophilic functional groups can be from 0.8:1.0 to 1.0:0.8. A person of ordinary skill in the art will recognize that additional ranges within these explicit ranges are contemplated and are within the present disclosure.

The solid contents of the blended precursor solutions can influence the properties of the resulting hydrogel as well as the ability of the precursor solution to fill the target space prior to crosslinking. If the solid content is too low, the hydrogel can be more susceptible to dilution effects from fluid present in the space at the time of delivery of the precursor solution. Even if the space is drained, there often can be significant amounts of residual fluid present. Dilution effects can inhibit desired space filling, can lead to irreproducible results, and can result in incomplete crosslinking that results in a low modulus hydrogel implant. Excessively high solid content can result in a precursor solution that crosslinks too quickly and that has a viscosity that is higher than desired, which can result in clogging of the applicator and/or incomplete filling of the targeted space. Note that the viscosity changes quickly due to the fast gelation times, and once gelled, the viscosity is essentially infinite. Generally, the blended precursor solution delivered form the applicator has a solid content from about 3 weight percent (wt %) to about 20 wt %, in further embodiments from about 3.5 wt % to about 18 wt %, and in other embodiments from about 3.75 wt % to about 16 wt %. A person of ordinary skill in the art will recognize that additional ranges within the explicit ranges above are contemplated and are within the present disclosure.

To achieve the target percent solids, the two precursor solutions can in principle have selected volume ratios. Generally, it is simplest to use equal volumes of the precursor solutions and the accelerator solution since then syringes or other reservoirs can correspondingly have equal volumes and consistent delivery. Nevertheless, the volume ratios and concentrations can be adjusted to yield the same mixed concentrations. Based on selected solid percent, desired volumes and volume ratios, the precursor solution concentration follows accordingly.

For the electrophilic macromers or macromers with amine groups, the polymers can have a plurality of arms each with a terminal functional group suitable for crosslinking. As noted above polyethylene glycol (PEG) based macromers are established hydrogel precursors and core compounds are commercially available. PEG is also know in the art as polyethylene oxide (PEO), and these names are interchangeable. The PEG cores can have 3, 4, 5, 6, 7 8, 9, 10 or more arms and 4 arm (4A) and 8 arm (8A) PEG are convenient degrees of branching. The macromers can also have selected molecular weights, and suitable ranges can be from 10,000 Da (10 kDa) to 100,000 Da (100 kDa).

In general, the precursors (electrophiles and nucleophiles) are generally shipped in separate sterile vials. At an appropriate point in a procedure, such as at the beginning of the procedure, these are mixed and loaded into the syringe. Various configurations of the vials and other sterile components can be provided to facilitate this processing. Depending on the anticipated time of use, the pot life can be appropriately tracked.

Accelerator Solution

In some embodiments, the crosslinking reaction might occur slowly under neutral conditions, but the addition of an accelerator, such as a basic buffer, accelerates the reaction such that it occurs over a desirable time frame. Thus, for the hydrogels of particular interest herein, suitable buffers are near a neutral pH although somewhat basic, and can include, for example, borate, phosphate, citrate, bicarbonate, CHES (N-Cyclohexyl-2-aminoethanesulfonic acid), TAPS ([tris (hydroxymethyl)methylamino]propanesulfonic acid), Bicine (2-(bis(2-hydroxyethyl)amino)acetic acid), Tris (tris (hydroxymethyl)aminomethane), Tricine (N-[tris(hydroxymethyl)methyl]glycine), CAPS (N-cyclohexyl-3-aminopropanesulfonic acid), CABS ($C_{10}H_{21}NO_3S$), CAPSO ($C_9H_{19}NO_4S$), or the like. The selected hydrogel precursors can be initially mixed to have a pH near neutral to slightly acidic to provide for slow crosslinking until mixed with the accelerant buffer.

Mixed buffers can be particularly desirable for accelerator solutions. Mixed buffers are known to extend the range of buffer capacity relative to the individual buffers. The mixed buffers for the accelerator solutions are able to provide desired basic pH values but then transition to more neutral pH values following completion of the crosslinking. So the pH is maintained to complete the crosslinking, but with moderate buffer capacity. Generally, one of the mixture have a relatively high pKa, e.g., above 9, such as borate or CHES, while another buffer has a more neutral pH, such as phosphate or citrate. The relative amounts of the two or more buffers are not particularly limited as long as the desired pH values are achieved. Total buffer concentration ranges for some embodiments are given below. In some embodiments, the weight ratio of the more neutral buffer to the more basic buffer can be from about 0.05 to about 2.5, in further embodiments from about 0.2 to about 2.25 and in some embodiments from about 0.25 to about 2. A person of ordinary skill in the art will recognize that additional ranges within the explicit ranges are contemplated and are within the present disclosure.

Suitable crosslinking times vary for different applications. In most applications, the crosslinking reaction leading to gelation occurs within about 5 minutes, in some embodiments, within about 1 minutes, and in further embodiments from about 2 second to about 30 seconds from initiation of delivery to gelation. A person of ordinary skill in the art will recognize that additional ranges of gelation time within the explicit ranges above are contemplated and are within the present disclosure. These gelation times do not necessarily correspond with full crosslinking which can occur over a longer time period, but the gelation times correspond with reaching a point of crosslinking in which the hydrogel no longer is flowable. Crosslinking times for in situ systems are a combination of several factors, including relative concentrations of reactive precursors, the molar ratios of the reactive ends, temperature, and resulting pH after mixing. Full crosslinking can occurs in some embodiments after about 10 minutes, and in further embodiments after about 15 minutes.

Gel times may be varied by altering the pH, temperature, and buffer salt strength of the "accelerator" portion of the in situ system. In one embodiment, the pH range used to accelerate the system is pH about 7 to 12. In further embodiments, the pH range is about 8 to 11, in some embodiments, in a pH range from about 9 to 10.5, and in additional embodiments, in a pH range from about 9.5-10.25. In one embodiment, the total accelerator buffer salt concentration ranges from about 50 mM to about 1.5M. In some embodiments, the buffer salt concentration is from about 100 mM to about 1M, and in further embodiments from about 150 mM to 700 mM. A person of ordinary skill in the art will recognize that additional ranges of pH and concentration within the specific ranges above are contemplated and are within the present disclosure.

Delivery Systems For Forming Hydrogel Implants In Situ

The delivery systems taught herein provide for desired functionality for delivery of the polymer. Specifically, the applicator can incorporate a design in which compositions from separate syringes are actively mixed and then directed to a narrow tube or catheter. For transcervical delivery, a specific applicator is described to provide for convenient, accurate and reproducible delivery is described. Further details on this device are provided in the '792 application cited above. An alternative design for laparoscopic polymer delivery is also described.

Referring to FIG. 1, an illustrative delivery system constructed in accordance with the principles of the protocols herein is described. Delivery system 100 comprises single-lumen catheter 108 having proximal end 110 and distal end 101. Proximal end 110 is attached to a Y connector 112 through a fitting 111, such as standard luer lock fitting. Y connector 112 can comprise a static mixing element, such as within tubing segment 113. Catheter 108 has an installation tip 102 at the distal end 101. In some embodiments, an egress limiter 106 is adjustable, such as being slidable along catheter 108 to adjust the length of catheter segment 104, distal to the egress limiter 106. As shown in FIG. 1, the length of catheter 108 from the distal end of installation tip 102 to the proximal end of egress limiter 106 may be from about 5 cm to about 15 cm. In some embodiments, the length may be from about 7 cm to about 10 cm. Also shown in FIG. 1, the length of the catheter from the proximal end of egress limiter 106 to the proximal end of fitting 111 may be approximately 4 cm to about 20 cm. In some embodiments, the length may be from about 7 cm to about 9 cm. One of ordinary skill in the art will appreciate that the selected length of the catheter and the presence and/or position of the egress limiter generally depends on various factors, such as the patient's anatomy, the application conditions, and the practitioner's preferences and that additional ranges of values within the explicit ranges above are contemplated and are within the present disclosure. For example, a practitioner may choose a longer catheter for a laparoscopic procedure than for a transvaginal procedure and this preference could be accommodated by using a longer catheter length while independently maintaining a medically appropriate length of catheter segment 104, which can be adapted from the more specific teachings for a cervical approach by a person of ordinary skill in the art. For commercial devices, generally various catheter lengths can be available for selection by the health care provider that can be connected to fitting 111, although in some embodiments described below, the length is adjustable such that the same components can be used to provide different lengths from the egress limiter to the distal end. Egress limiter 106 may have a conical, as shown, or other shape to act as a backstop or flow limiter for the prevention of excess material run off during the hydrogel application as well as to guide the health care professional for placement at the selected position. Mixing of a first solution 114 and a second solution 116 occurs within Y connector 112. Y-connector 112, in its outflow channel, or a separate section of tubing segment 113 connected to the Y-connector can comprise a static mixing element that has flow-altering baffles to encourage appropriate mixing of the solutions. Y-connector 112 has a fitting 111, such as a Luer connector for attachment of catheter 108, and connections to syringes 115, 117, which may or may not be releasable. First solution 114 generally is a mixture of a first precursor and a second precursor formed at an appropriate time such that the reaction does not occur to an undesirable amount during relevant time scales without an accelerator, and respectively, the second solution generally is an accelerator/catalyst. Syringes 115 and 117 generally are held via a molded syringe holder 118 or the like to provide for convenient handling by the health care professional during use. An optional fixed ratio of solution delivery ratio can be maintained by an optional plunger cap 120. If the internal diameters of syringes 115, 117 are the same, movement of plunger cap 120 would deliver a 1:1 ratio of volumes, but the internal diameters can be selected to provide a different volume ratio if desired. The outer diameters of syringes 115, 117 may or may not track the inner diameters depending on the syringe wall thicknesses.

Delivery system 100 and components thereof may be fabricated of any of a wide variety of materials that are sufficiently flexible and biocompatible as appropriate, and different components can be assembled from appropriate materials for that component. Some components can be readily adapted from commercially available parts. For example, polyethylenes, nylons, polyvinylchlorides, polyether block amides, polycarbonates, polyurethanes, polyolefins, polysiloxanes and other similar materials are suitable. In some embodiments, the delivery system comprises a soft installation tip material to reduce traumatic injury to the uterine surface during insertion and injection of the mixed fluid, and materials for the installation tip are described further below.

Figure 2:
FIG. 2 is a cross-section of a basic installation tip of the hydrogel applicator of FIG. 1.

FIG. 2 is a fragmentary view of a basic tip 126 for installation tip 102 of catheter 108 (see FIG. 1). Tip 126 has an open end to a cylindrical catheter. Catheter 108 may be configured to have an installation tip 102 with one or multiple side ports and/or one or multiple terminal exits. The side port(s) and/or terminal exit(s) can be configured to facilitate the uniform delivery of the mixed fluid into the uterine cavity. The installation tip 102 generally is flexible and configured to be atraumatic during use, and suitable materials are described below.

Figure 3:
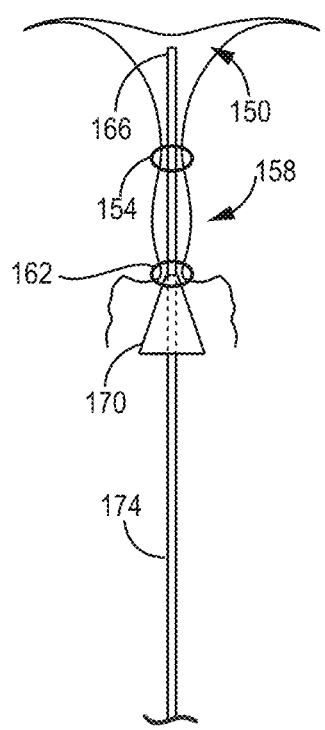
FIG. 3 is a depiction of a hydrogel applicator being used to deliver a medical grade hydrogel system to the uterus through the cervix, with the cap element being used to control catheter placement and egress of material from the external cervical os.

FIG. 3 shows uterine cavity 150, installation tip 166, internal os 154, endocervical canal 158, which is approximately 4 cm in length, external os 162, cap element 170, and catheter 174. Generally, for a particular patient, the health care provider knows with reasonable accuracy the patient's uterine anatomy relating to the uterine length and the length of the endocervical canal such that a closure on the catheter can be adjusted to provide the prescribed distance of the catheter tip from the back of the uterus. The distance from the catheter tip to the back of the uterus following placement of the catheter can be from about 0.25 cm to about 2.0 cm and in further embodiments form about 0.35 to about 1.25 cm. A uterine sound instrument can be used to evaluate the distance using conventional procedures, and the sound can be held next to the egress limiter to adjust the position of the cap. A person of ordinary skill in the art will recognize that additional distance ranges within the explicit ranges above are contemplated and are within the present disclosure.

Figure 4:
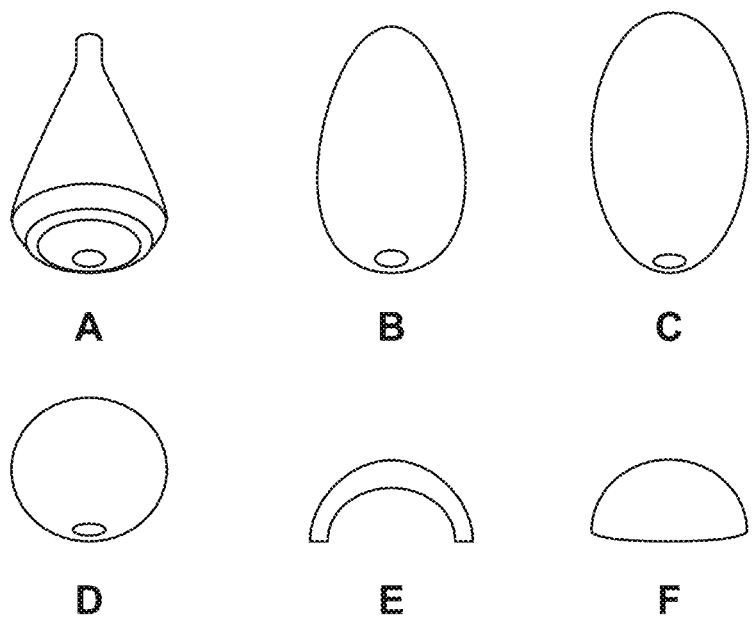
FIG. 4 is an illustration of various cap element designs.

FIG. 4 shows various embodiments of cap element 109 which are shaped to act as a backstop or cervical cap for the prevention of excess material run off during the hydrogel system fluid delivery, as well as reference guide for the placement of installation tip 102. In this context, cap element 109 of egress limiter 106 can be generally highly curved with no sharp points, and it has a radial extended diameter relative to catheter 108. FIG. 4 shows (A) a conical-shaped, (B) a tear drop-shaped, (C) an egg-shaped, (D) a sphere shaped, (E) a flattened hemisphere-shaped, and (F) a dome-shaped cap elements. Embodiments with a dome-shaped cap element can be used to provide a concave seal against the exocervix. The egress limiter design can be selected to meet the desired function to seal the endocervical canal 158. Generally, such an object may be circular, conical or angled one or more surfaces to ensure a secure fit within the outer opening into the cervix, to allow a complete coating of the lumen of the uterus and at least inner portion of the cervix through stabilization of the hydrogel in the enclosed volume as the hydrogel sets sufficiently to avoid loss through the cervix, allowing for a gently pressurized tamponade-like fill of the hydrogel if desired. Thus, cap element 109 can have a radial diameter relative to the catheter axis from about 5 mm to about 1.5 cm and a length along the catheter axis from about 2 mm to about 4 cm and in some embodiments from about 4 mm to about 3 cm. A person of ordinary skill in the art will recognize that additional ranges within the explicit dimensional ranges are contemplated and are within the present disclosure. Cap element 109 can be formed from any appropriate material, such as polymers including, for example, the polymers suitable for the catheter and the installation tip.

Installation tip 102 desirably presents an atraumatic structure to the patient, which can be characterized by a softness and flexibility. In some embodiments, an atraumatic tip can be formed from elastomers, such as silicone rubbers, rubber, polyisoprene, butyl rubber, mixtures thereof and the like. In additional embodiments, the atraumatic tip can be a second material to the primary catheter shaft material cojoined to the distal end through radiofrequency welding, melting, gluing, or other know methods of attachment. In other embodiments, the atraumatic tip involves a coating added to the end via attachments of different materials or overlay of a coextruded soft flexible material. Materials for the atraumatic tip can be characterizes with respect to their softness using Shore Durometer values and may be possess Shore Hardness 00 values of 20 to 80, with further embodiments in the 00 scale 50 to 70 range. For embodiments in which the transcervical access system may be used to extract fluid, a catheter with a harder tip can be used. A person of ordinary skill in the art will recognize that additional ranges of durometer values within the explicit ranges above are contemplated and are within the present disclosure.

Figure 5A:
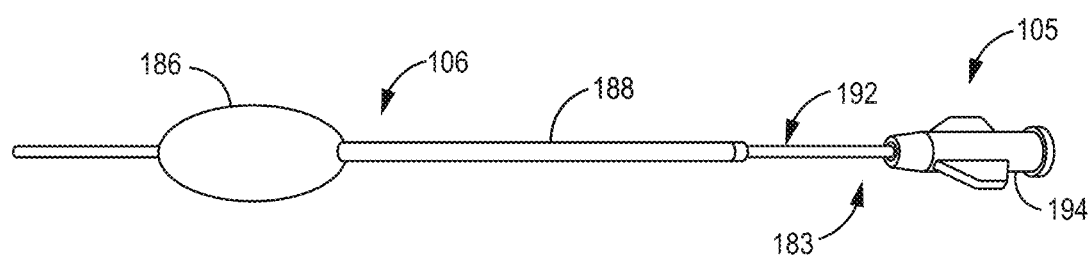
FIG. 5A is a depiction of an assembled configuration of a catheter and an egress limiter.
Figure 5B:
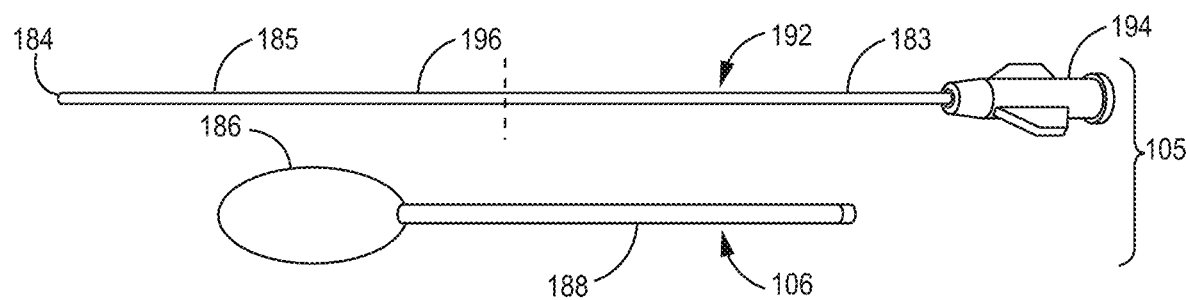
FIG. 5B is a depiction of a separated configuration of a catheter and an egress limiter of FIG. 5A.

FIG. 5A shows an embodiment in which catheter assembly 105 has catheter 192 and egress limiter 106. Egress limiter 106 comprises cap element 186 and tubular member 188 proximal to cap element 186. Tubular member 188 is supported by the catheter during infusion and is generally less flexible than the length of catheter 192 distal to cap element 186. FIG. 5A depicts the assembled device, while FIG. 5B depicts separated catheter 192 and egress limiter 106. Catheter 192 comprises a connector or hub 194 and a tubular element 196. Length of catheter 192 is designed for insertion into the uterine cavity with cap element 186 against the outer opening into the cervix, referred to as the external orifice or external os. Tubular member 188 can have an adjustable position when assembled to correspond with overlapping all or a portion of the length of tubular element 196 from cap element 186 to connecter 194. Furthermore, tubular element 196 may or may not be uniform along its length with respect to structure and/or composition. As noted above, the catheter tip can be very soft to avoid tissue injury during hydrogel infusion, but a very soft polymer can make manipulation of the applicator more difficult if incorporated along the entire length of tubular element 196. In some embodiments, tubular element 196 comprises a distal port 184 and in some embodiments includes a tip, and a proximal portion 183 that is stiffer than distal portion 185, which is shown with a dashed line to divide these regions. Optional positions for separating a stiffer proximal region is described further below. Proximal portion 183 can be formed from a section of tubing secured over the catheter, a change in material of the catheter, and/or a thickening of the catheter wall. The embodiment with a stiffer proximal section 183 depicted in FIGS. 5A and 5B gives the user greater stability when instrumenting the endocervical canal.

Referring to FIG. 5A, the proximal end of cap element 186 is attached to tubular member 188 to provide egress limiter 106, as shown in a separated configuration in FIG. 5B. In the assembled configuration of FIG. 5A, tubular member 188 provides external stiffening to at least a part of the length of catheter 192 proximal to the cap element. Tubular member 188 also allows for gripping egress limiter 106 to facilitate the procedure. Tubular member 188 can have a length from about 5 cm to about 20 cm, in further embodiments from about 6 cm to about 19 cm, and in some embodiments from about 7 cm to about 18 cm. A person of ordinary skill in the art will recognize that additional ranges of length within the explicit ranges above are contemplated and are within the present disclosure. The egress limiter 106 is engaged over part of catheter 192 as shown in FIG. 5A, generally for insertion of the catheter into the patient. The egress limiter 106 allows the user to adjust the position of cap element 186 to give values of the distal catheter length in the ranges as specified above. In some embodiments, tubular member 188 can internally provide a friction interaction with the catheter surface to restrict unintended motion of the positon of egress limiter 106. The user can set the position of egress limiter 106 and maintain the position along the catheter 192 by avoiding unintended sliding of tubular member 188. In other embodiments, the cap element 186 position can be adjusted and/or maintained via a clip, ridges that engage a flange on the mated element, or the like between catheter 192 and egress limiter 106. Since the cap element 186 is fixedly attached to the tubular member 188, the design of tubular member 188 prevents the inadvertent loss of the cap element 186.

Figure 6B:
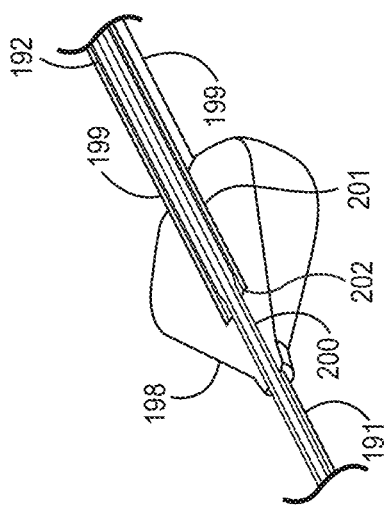
FIG. 6B is an enlarged cross-section of a portion of the catheter assembly and egress limiter of FIG. 6A.
Figure 6A:
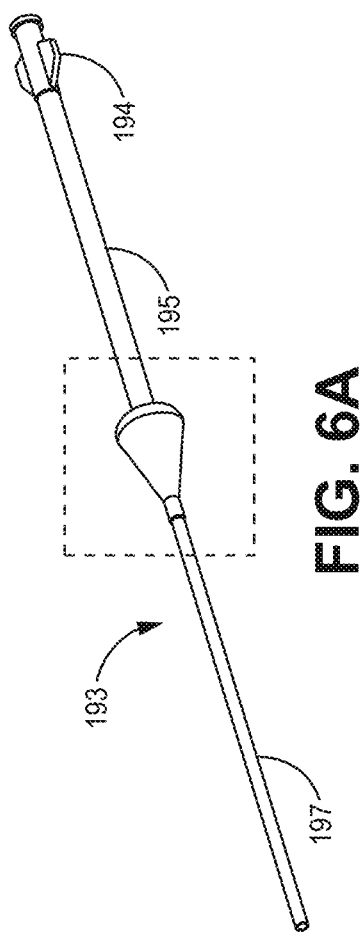
FIG. 6A is an illustration of a catheter assembly with an egress limiter and connector for use with the hydrogel delivery systems described herein.
Figure 6C:
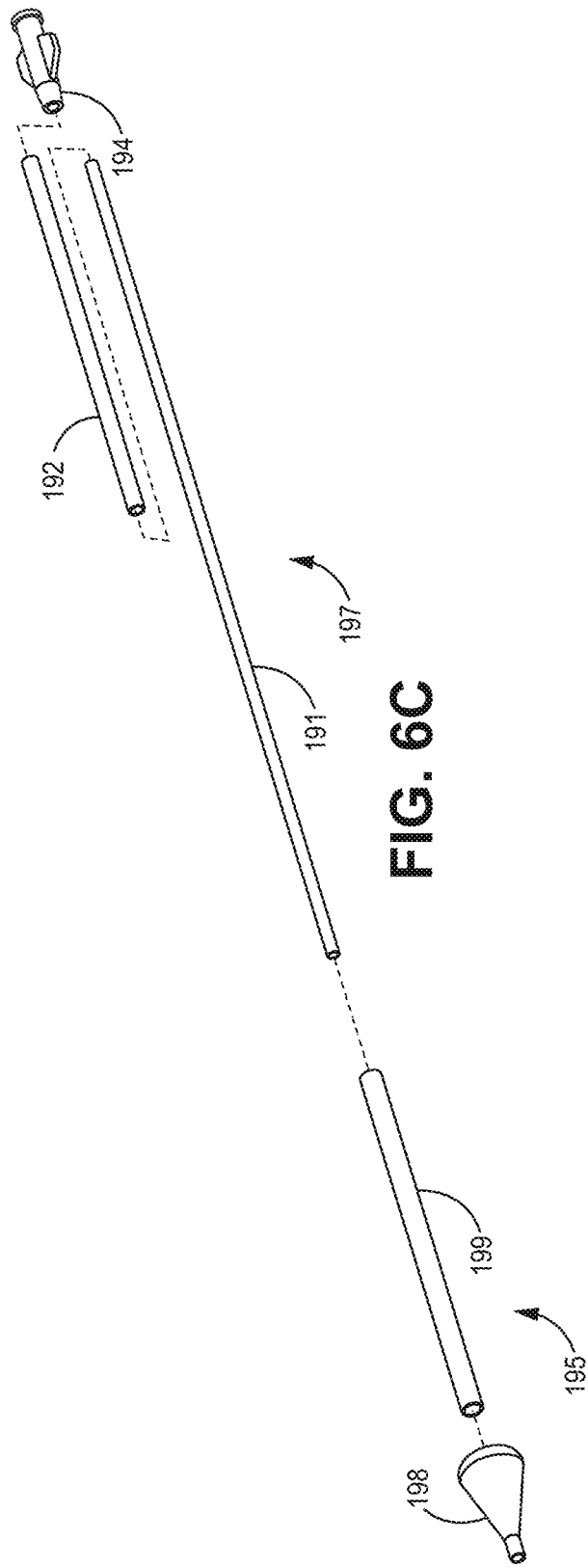
FIG. 6C is an exploded view of the catheter assembly, egress limiter, and connector of FIG. 6A.

FIG. 6A shows a specific embodiment of a catheter assembly 193 comprising a catheter 197, an egress limiter 195 and connector 194. FIG. 6B shows an enlarged cross-section of the portion of FIG. 6A as indicated by the dashed box. FIG. 6C shows an exploded view of catheter assembly 193. Catheter 197 comprises core tube 191 and overtube 192, both of which engage and are secured to connector 194, which can be a female luer connector or the like. As assembled, catheter 197 has a distal section with a smaller diameter than a proximal section due to the presence of the overtube. Connector 194 can be secured with adhesive, heat bonding, crimping, a combination thereof, or the like, as long as the central lumen remains open. Overtube 192 can be held in place just through securing to connector 194, or also with heat bonding, adhesive bonding or other suitable technique(s) to core tube 191. Overtube 192 provides stiffness to the proximal end of catheter 197 and can provide frictional engagement of egress limiter 195. Overtube 192 can be made thicker and/or with a stiffer material relative to core tube 191. In some embodiments, overtube 192 can have a length from about 5 cm to about 20 cm, in further embodiments from about 6 cm to about 19 cm, and in some embodiments from about 7 cm to about 18 cm. A person of ordinary skill in the art will recognize that additional ranges of length within the explicit ranges above are contemplated and are within the present disclosure.

Referring to FIG. 6C, egress limiter 195 comprises conical cap element 198 and tubular member 199. Conical cap element 198 is attached to tubular member 199 with adhesive or other suitable fastening modality. Referring to FIG. 6B, conical cap element 198 has a cavity with distal diameter 200, proximal diameter 201 and step-down 202. At step-down 202, the cavity diameter within the conical cap element decreases. Step-down 202 provides a mechanical stop to inhibit sliding of egress limiter 195 in a more proximal direction relative to overtube 192. Conical cap element 198 can have a narrow constriction at its distal end to provide a friction grip on catheter 197 that constrains movement of egress limiter 195 along the catheter so that the position can be selected by the medical professional, although friction with overtube 192 can provide itself the desired limits on relative movement of egress limiter 195.

Procedures

The hydrogel applicator in it various embodiments is particularly effective for the delivery of the various hydrogel systems described herein.

Figure 7:
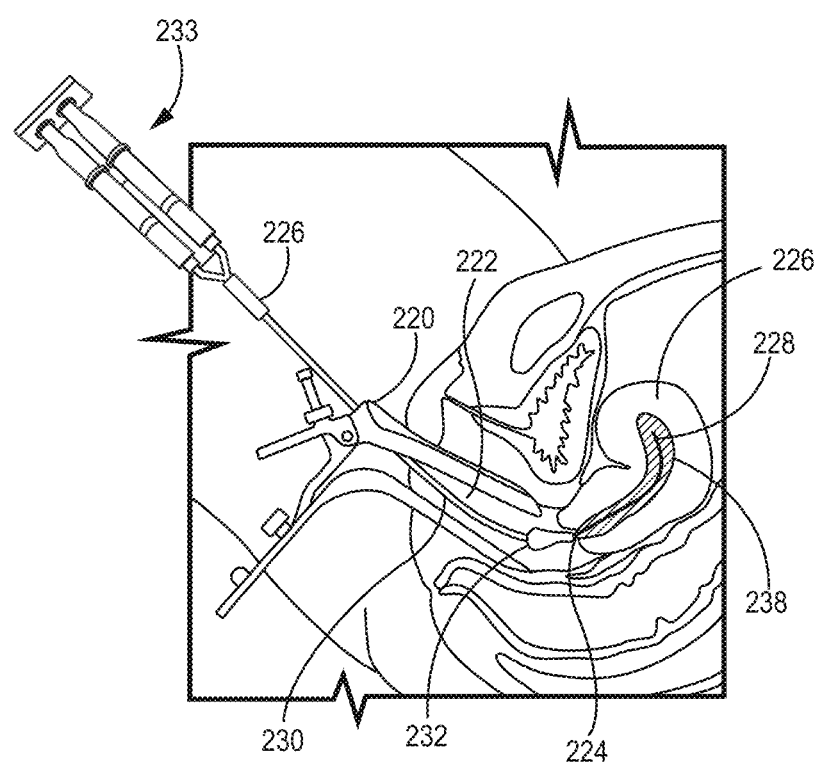
FIG. 7 is a depiction of a hydrogel delivery system being used to transcervically deliver a hydrogel polymer composition to the uterus.

FIG. 7 illustrates a procedure in which the hydrogel is installed into the uterus transcervically. Vaginal speculum 220 is inserted into vagina 222 to dilate vagina 222. The installation tip 228 of catheter 230 is guided through vagina 222 and cervix 224 and into uterus 226. Installation tip 228 is flexible at the distal end which allows installation tip 228 to adjust to the shape of uterus 226 and reduce risk of trauma. Cap element 232 is positioned a distance from the distal end of installation tip 228 to limit depth of insertion of installation tip 228 into the uterus. In one embodiment, cap element 232 is adjusted to an appropriate distance from the distal end of installation tip 228 so that the medical practitioner can comfortably operate the syringe when installation tip 228 is positioned with cap element 232 adjacent the opening into the cervix with the tip spaced an appropriate distance from the back wall of the uterus. In some embodiments, cap element 232 is part of an adjustable egress limiter. In some embodiments, catheter 230 with cap element 232 is installed into uterus 226 by the practitioner without syringe assembly 233 attached, then syringe assembly 233 is attached to catheter 230, such as via luer connector 226, in a subsequent step. In some embodiments, a regular empty syringe can be first placed on luer connector 226 to withdraw fluid from the uterine cavity, and following completion of this fluid removal, the syringe can be removed and replaced with syringe assembly 233. Such a stepwise procedure may facilitate single user insertion and application. As discussed above, for appropriate embodiments, the cap element may be adjusted and/or fixed in a position along the catheter length by manually adjusting the proximal end of the egress limiter. When positioned adjacent the opening into the cervix, cap element 232 may function to plug the uterine cavity for through filling and coating with hydrogel. This allows the practitioner a means to inhibit leakage of instilled hydrogel at the external cervical os. Additionally, for some embodiments, cap element 232, if inflatable, may be further adjusted to fit within the cervix by filling with fluid, such as gas or liquid.

For any embodiment of cap element, a distance marker along the catheter can help to position cap element 232 at the proper location for installation. After installation tip 228 and cap element 232 are placed as desired, syringe assembly 233 is used to introduce one or more precursors and, if applicable, an accelerator solution into the Y connector (optionally containing a static mixing element) to provide a mixed hydrogel forming composition prior to entry into catheter 230. The mixed fluids remain sufficiently fluid until they exit installation tip 228 and then further polymerize and/or crosslink to form a hydrogel 238 that occupies the uterine cavity. In some embodiments, injection is continued without stopping until completed so as to prevent plugging of the catheter 230 and/or the installation tip 228 due to the hydrogel formation. In some embodiments, syringe assembly 233 comprises a plunger cap to facilitate the appropriate volume ratio dispensing from the two syringes.

An outline of an embodiment of procedures particularly suitable for the hydrogel compositions and applications of particular interest are presented below. For these embodiments, it is envisioned that the two hydrogel precursors (PEG-based precursor & crosslinker) are premixed together, and the time from the mixing until delivery can be referred to as the pot life. The two precursors can be provided in suitable containers to facilitate their mixing. One of the precursors or a separate solution mixed with the precursors can comprise a visualization agent. The mixed precursors with optional colorant are loaded into a syringe or the like. Based on the selected precursors, the crosslinking of the precursors occurs slowly at the pH of the mixed precursors. A second syringe is provided with a buffer, generally clear solution that is mixed with the precursors to begin acceleration of the crosslinking during the delivery process. This discussion is directed to steps 1 and 2 below.

The following method of delivery may be advantageously used to form the intrauterine hydrogel barrier:

1) Mix diluent (blue) with PEG, dissolve.
2) Draw PEG solution back into syringe.
3) Attach Y connector to each syringe
4) Load clear and blue syringes into syringe holder
5) Put plunger cap on syringe ends. Set down.
6) Position flow limiter to correct depth on catheter shaft, ensuring that when the flow limiter is against the cervical external os the distal catheter tip will be about 1 cm below the uterine cavity fundus.
7) Attach syringes with Y connector to applicator.
8) PRIOR TO 60 MIN ELAPSED FROM STEP 1, insert catheter into the uterus via the cervix until the flow limiter is against the cervical external os.
9) While applying gentle pressure on the flow limiter against the cervical os, continuously deliver hydrogel through pressing the applicator cap at a relatively constant force until the syringes are empty. Most uterine cavity sizes will not require the full amount of hydrogel so colored fluid will be seen exiting the cervix at the point where the flow limiter is placed and providing sight slight resistance to the flow.
10) Wait roughly 2 seconds and gently remove catheter.

Once the syringes are prepared, they can be attached to the Y-connector, generally using standard connectors, such as a luer fitting, 3) above. To allow for convenient delivery, the syringes are generally placed in a syringe holder (step 4) above) to allow for handling with one hand, and a plunger cap can be placed to allow for the uniform delivery of liquid simultaneously from both syringes possibly using one hand. The applicator tip can be inserted into the patient to the desired depth, which may be marked with an acorn or the like. If desired the applicator tip can be placed before the syringes are fully prepared.

With the applicator tip in place, the uterine cavity can optionally be flushed to remove blood, fluids and potential other materials left from the procedure. For example, a syringe or the like with a flush solution, such as buffered saline or other desired liquid, can be attached to the connector of the applicator tip, for flushing. Although use of the applicator tip can be desirable, flushing can be performed using a different channel, possibly prior to placement of the applicator tip. Flushing can be performed with a selected amount of fluid, or continued until the discharge seems to have cleared the space.

When ready for the delivery of the hydrogel precursors into the uterine cavity, the Y-connector can be attached to the connector of the applicator tip, step 7). In alternative embodiments, if the applicator tip is not used for flushing, the Y-connector can be attached to the applicator tip prior to placement of the applicator tip into the patient. The hydrogel precursors are then delivered into the patient, step 8). The syringe cap generally is pushed relatively continuously so that excessive crosslinking does not take place in the applicator tip, although strict continuous delivery is not needed. The rate of delivery can be approximately constant, but again this is not required or even necessarily desired if the force for delivery changes as the cavity fills. In some embodiments, it is desirable to begin delivery of the hydrogel prior to the pot life exceeding 60 minutes. For alternative hydrogel formulations, this time may be altered.

The fluid delivery can be continued until pressure from the uterus pushes back against the acorn. The push back would suggest that the uterine cavity is full with fluid. When the cavity is full, injection is stopped. After stopping the delivery, it is desirable to wait a short period to allow for crosslinking and gelation to take place. After waiting for a reasonable period of time, such as about 2 seconds and less than 5 minutes, the applicator tip is removed, step 10). With sufficient crosslinking, little if any hydrogel should be lost from the uterine cavity. The completeness of the hydrogel delivery can be confirmed using ultrasound.

Figure 8:
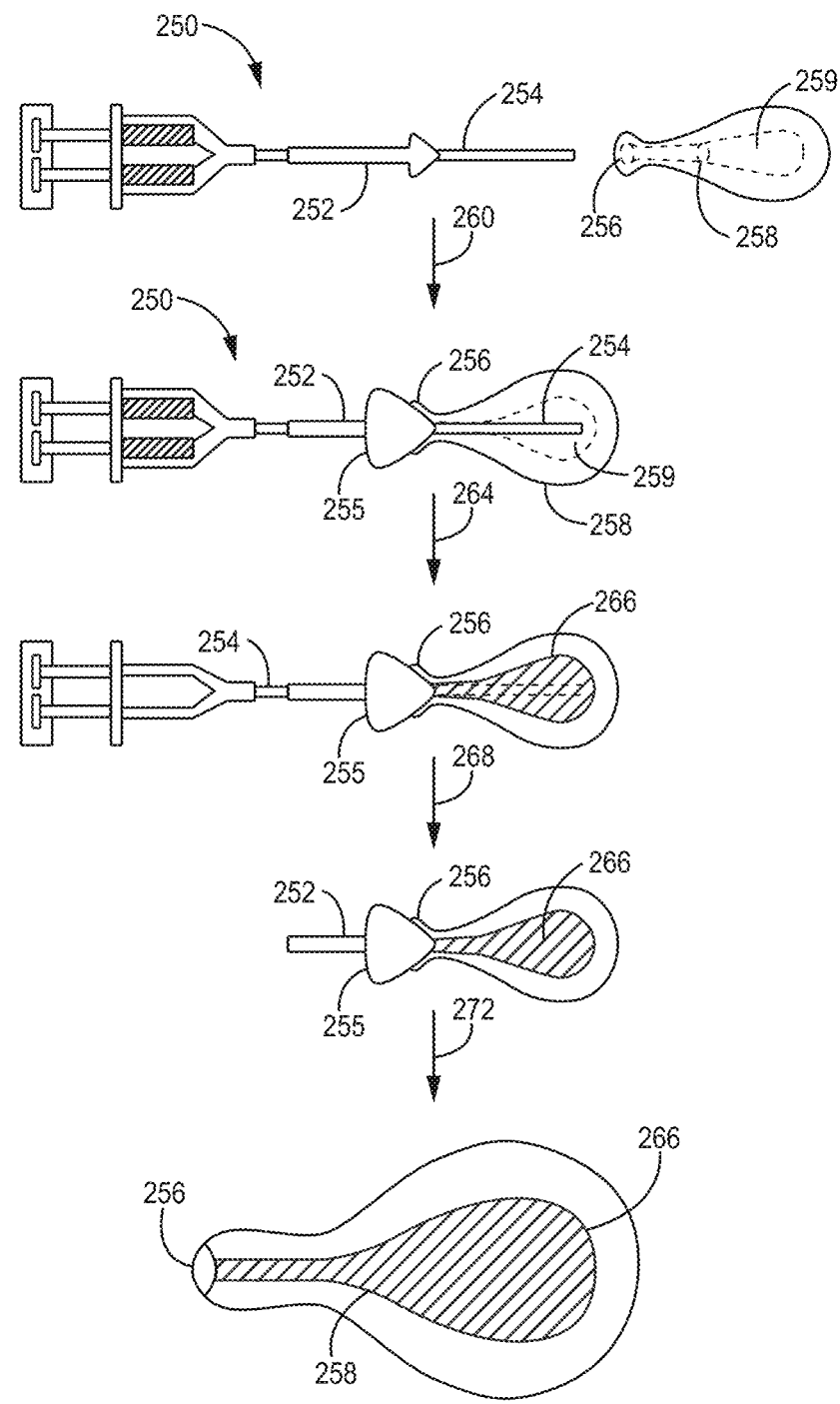
FIG. 8 is a depiction of a transcervical procedure using a hydrogel delivery system with an egress limiter to fill the uterus with a hydrogel polymer composition.
Figure 9:
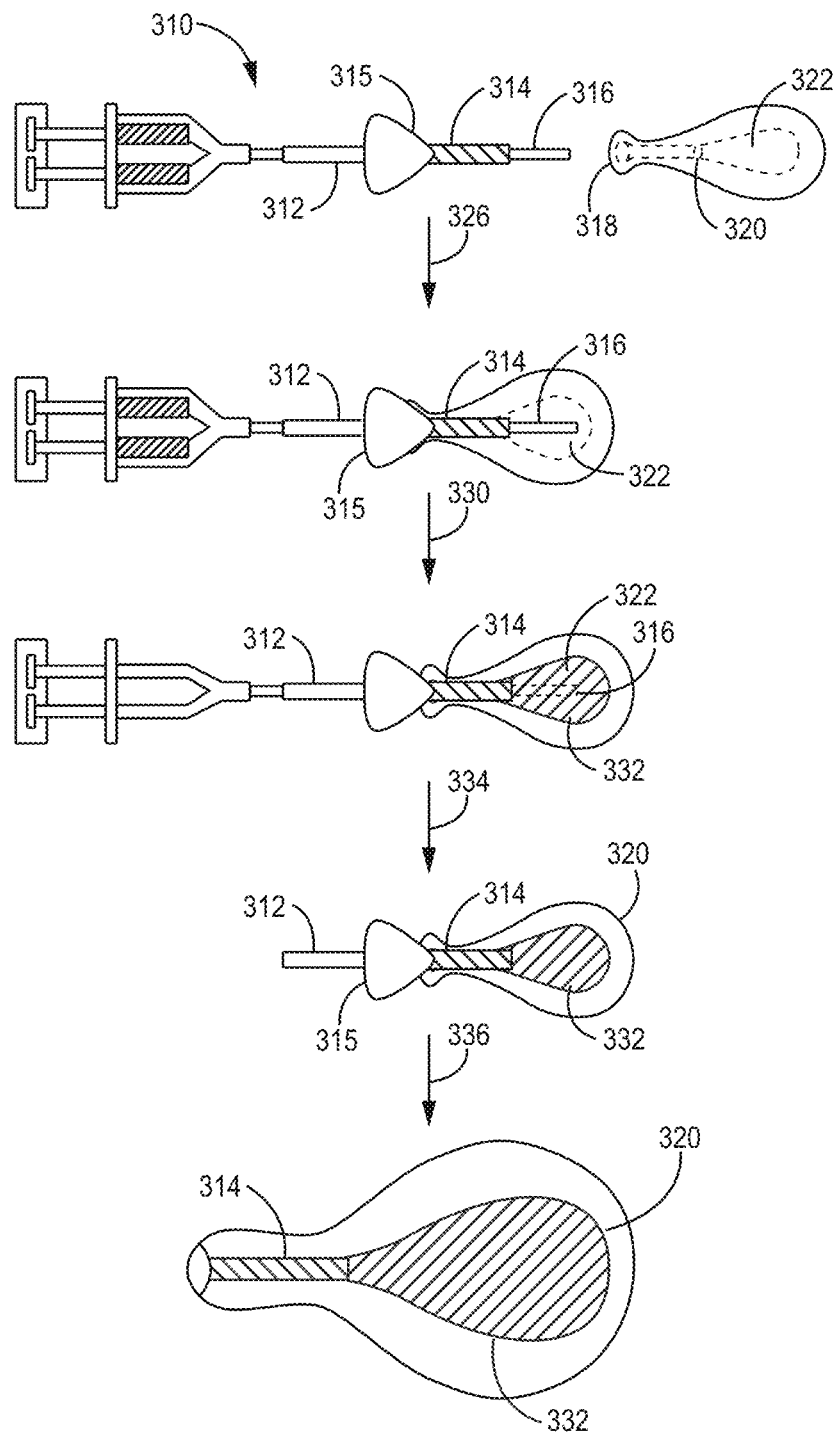
FIG. 9 is a depiction of a transcervical procedure using a hydrogel delivery system with a cervical plug and an egress limiter to fill the uterus with a hydrogel polymer composition.

FIGS. 8 and 9 depict transcervical hydrogel delivery using various embodiments of the improved procedures based on the hydrogel systems described herein, with FIG. 8 based on a removable egress limiter and FIG. 9 directed to use of both a removable egress limiter and a cervical plug. These figures are presented as procedural flow diagrams with procedural flow progressing from top down.

Referring to FIG. 8, in this embodiment, the transcervical applicator takes the form of applicator 250, which is depicted with egress limiter 252 mounted on catheter 254 aligned for insertion 260 through the cervical outer os 256 past cervical inner os 258 into uterus 258 within uterine cavity 259. Following insertion 260, cap element 255 is positioned at outer os 256 and catheter 254 is within uterine cavity 259, as shown in in the second drawing in FIG. 8. Hydrogel precursor is injected 264 into the uterine cavity to fill the cavity with hydrogel 266. Catheter 254 is then removed 268, as shown in the fourth drawing of FIG. 8, while leaving egress limiter 252 with cap element 255 at outer os 256. Removing 272 egress limiter 252, the last figure of FIG. 8 shows uterus 258 filled with hydrogel 266 extending past inner os of the cervix.

Referring to FIG. 9, the top image depicts an applicator 310 with a egress limiter 312 and a cervical plug 314 distal to the cap element 315 of egress limiter 312 mounted over catheter 316 positioned for insertion into outer os of the cervix into the uterus 320 for placement of the catheter tip in the uterine cavity 322. Following insertion 326, the second image of FIG. 9 shows the tip of catheter 316 in uterine cavity 322 with cervical plug 314 in the cervix and cap element 315 positioned at the outer os of the cervix. Following injection 330 of hydrogel precursors, the third image of FIG. 9 depicts hydrogel 332 within uterine cavity 322 up to cervical plug 314. Following removal 334 of catheter 316 from uterus 320, hydrogel 332 fills the uterus, cervical plug 314 is in place within the cervix, and egress limiter 312 is in position with cap element at the outer os of the cervix. Following removal 336 of egress limiter 312, the last image of FIG. 9 depicts uterus 320 filled with hydrogel 332 with cervical plug 314 still in place. For inter-uterine applications, the hydrogel systems can be suitable for transcervical delivery, delivery through a laparoscope at the end of a laparoscopic procedure, or for open procedures, generally with use during the closing steps of the procedure. The hydrogel can function as a tamponade as well as a material to reduce or eliminate adhesion formation. The design of the hydrogel properties to facilitate these function are described further below, while the delivery procedure using the applicators is described next.

Figure 10:
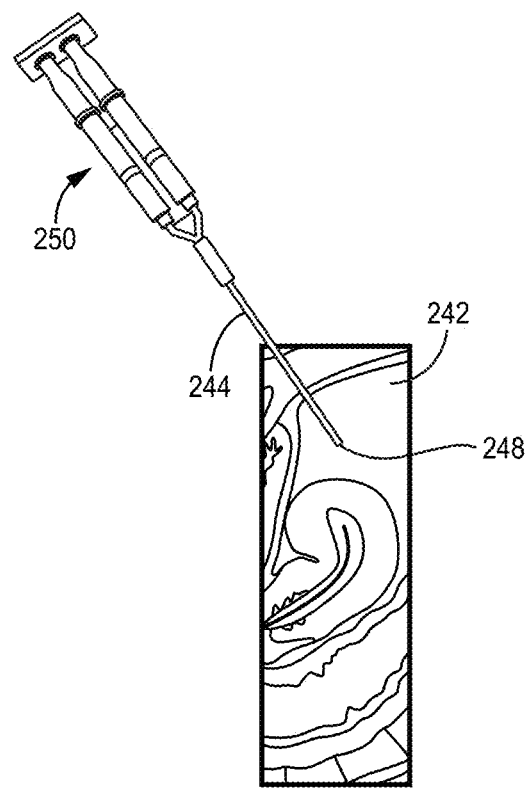
FIG. 10 is a schematic depiction of a hydrogel delivery system being used to percutaneously deliver a hydrogel polymer composition to a body cavity.

FIG. 10 illustrates a procedure in which hydrogel is installed into body cavity 242 laparoscopically, such as the pelvic cavity. Installation tip 248 of catheter 244 is placed in body cavity 242 via a hysteroscope channel and the mixed fluid is delivered into body cavity 242. As discussed above with respect to transcervical installation, syringe system 250 may be attached after or during placement of catheter 244. Other aspects discussed above also apply to laparoscopic installation of the hydrogel. Similarly, open procedures could be adapted for delivery of hydrogel to reduce or eliminate adhesions. For example, an open incision could be partially closed, followed by delivery of the hydrogel precursors, and then the closure of the incision can be completed.

As described in the Examples below, it has been observed for transcervical delivery that the hydrogel conformally filled the uterine space. It was also observed that the cornua was filled to the tubal ostium while the fallopian tubes remained clear of hydrogel. Similar results can be expected from laparoscopy procedures or open procedures.

The catheter length, inner diameter, outer diameter, and materials may vary depending on the access requirements. The catheter including the installation tip should be of a size appropriate to facilitate delivery, to have a low profile, and cause acceptably low trauma when inserted and advanced to a treatment site. In an embodiment suitable for forming hydrogel implants in the uterus, the installation tip has a distal outer diameter from about 1 mm to about 3 mm to allow delivery through the cervix. The proximal outer diameter of the catheter can be from about 2 mm to about 6 mm, in further embodiments form about 2.5 mm to about 5 mm, and in additional embodiments form about 2.5 mm to about 4.5 mm. The catheter length from the distal tip to connector can be from about 14 cm to about 30 cm, in further embodiments from about 15 cm to about 28 cm and in other embodiments form about 16 cm to about 26 cm. In some embodiments, the catheter OD should be as small as practical to reduce the size of the removal track after formation of the crosslinked gel in-utero. In other embodiments, the distal profile of the catheter to be placed within the cervix should be no more than 9Fr, in some embodiments no more than 8Fr, in additional embodiments from 3Fr to 7Fr. A person of ordinary skill in the art will recognize that additional length ranges and diameter ranges within the explicit diameter ranges above are contemplated and are within the present disclosure, such as 6 Fr, 5 Fr, 4 Fr. This reduces the need to withdraw during the injection event to prevent tunneling or removal of the barrier on device exit.

While the deployment of the hydrogel is often done without visualization and in a blind fashion, it is possible to add visualization agents, such as microbubbles to enable visualization under ultrasound or by adding a radiopacifying agent to enable visualization under X-ray guidance. These visualization agents may be mixed with the precursor solutions and/or covalently attached to one or both precursors. One embodiment involves using branched precursors that have a covalently attached radiopaque agent, so that the hydrogel will have the radiopaque agent covalently attached upon its formation from mixtures of, or including, the radiopaque-labeled precursor. In some embodiments, hyperechoic hydrogels may result from headspace in a precursor syringe and/or gas from the precursors being incorporated into the hydrogels as microbubbles. Ultrasound contrast may be increased or decreased by altering the headspace within the precursor syringes prior to gel installation.

Radiopaque agents may be attached to precursors by a variety of methods. Some of these methods are set forth in U.S. Pat. No. 7,790,141, which is hereby incorporated by reference herein for all purposes, and including radiopaque agents, precursors, and matrices; in case of conflict, this specification controls. Precursors set forth herein and in this incorporated reference may be decorated with one or more radiopaque agents. In the case of a branched or multifunctional precursor, one or more of the available reactive sites may be left unreacted. Thus an 8-armed precursor may have between 1 and 8 functional groups available for covalent binding to form a matrix and between 1 and 8 functional groups replaced by (or reacted with) radiopaque agents. Examples of radiopaque agents are molecules comprising iodine, TIB, phenyl ring compounds such as 2, 3, 5-triiodobenzoic acid, 3, 4, 5-triiodophenol, erythrosine, rose bengal, 3, 5-Bis(acetylamino)-2, 4, 6-triiodobenzoic acid, and 3, 5-Diacetamido-2, 4, 6-triiodobenzoic acid.

Additional machine-aided imaging agents may be used in addition to, or as alternatives to, radiopaque compounds. Such agents are, for example fluorescent compounds, ultrasound contrast agents, or MRI contrast agents (e.g., Gadolinium containing compounds). In some embodiments, suspended solid inorganic particulates, such as barium sulfate, titanium, and/or bismuth chloride, may be used to increase both radiopacity as well as visibility under ultrasound. In some embodiments, hydrogel particles may be incorporated into the hydrogel compositions. In some embodiments, particle composition, particle concentration, and particle size may be adjusted to tune the radiopacity and/or the ultrasound contrast of the hydrogel compositions. In some embodiments, particles may have an average diameter in a range from about 10 microns to about 500 microns. Particles with radiopaque agents may be blended with particles that are free of a radioopaque agent to make a collection of particles with a desired radiopacity.

In embodiments of particular interest, the hydrogel composition has a color agent to provide for convenient visual observation, as described further in the description of the hydrogels. If desired, the treatment space may be filled or flushed with a solution, such as an inert saline solution, to remove blood and other biological fluids from the treatment space prior to delivering the hydrogel. The delivery system 100 of FIG. 1 or the procedures of FIG. 7 or 10 optionally may include an additional lumen to permit such flushing liquids to exit the treatment space. Alternatively, a non-inert solution, such as a solution containing a pharmaceutical agent, may be delivered into the treatment space.

Hydrogel Properties

Hydrogels described herein generally can be delivered through less invasive means, such as a catheter with a small diameter. The hydrogel delivery system combines two solutions that are delivered as the blend that rapidly crosslink into the hydrogel. Thus, the hydrogel is fully formed in-situ after delivery. The hydrogels of particular interest generally begin as precursors that can react to form into a gel upon crosslinking by nucleophilic substitution. The polymer precursors are described in detail above.

The conditions can be controlled to obtain crosslinking and gel formation suitable for the delivery process using the applicators described above in the context of the delivery system. Generally, the crosslinking begins in the catheter of the delivery system, but does not complete sufficiently to limit flow from the catheter into the patient. The hydrogel can set sufficiently to remain in place in a reasonable period of time and can fully crosslink following completion of the procedure.

It is sometimes useful to provide color by adding a colored visualization agent to hydrogel precursors before crosslinking. The visualization agent may serve to help visualize the disposition of the hydrogel. For example, when filling a uterus, a visualization agent will help to distinguish the hydrogel from other fluids. Further, the hue of a colored hydrogel may provide information about the concentration of the precursors in the hydrogel or the degree of mixing of physiological fluids into the hydrogel. An embodiment of the invention uses biocompatible crosslinked polymers formed from the reaction of precursors having electrophilic functional group and nucleophilic functional groups. The precursors are generally water soluble, non-toxic, and biologically acceptable.

In an electrophilic-nucleophilic reaction system, a precursor comprises two or more electrophilic or nucleophilic functional groups, such that a nucleophilic functional group on one precursor may react with an electrophilic functional group on another precursor to form a covalent bond. If a precursor has more than two functional groups, the precursor molecule can participate in crosslinking reactions, and generally the hydrogels are relatively highly crosslinked. The small molecule crosslinker generally has a solubility of at least 1 g/100 mL in an aqueous solution.

A hydrogel for use on a patient's tissue that has water, a biocompatible visualization agent, and crosslinked hydrophilic polymers that form a hydrogel after delivery within the uterine cavity. The visualization agent reflects or emits light at a wavelength detectable to a human eye so that a user applying the hydrogel can observe the gel and also estimate its thickness.

The hydrogels for intrauterine placement generally have moderate swelling with sufficient swelling to facilitate filling the space but not excessive swelling to result in uncomfortable pressure on the patient. In some contexts, swelling can refer to continued volume or weight changes following initial formation of a crosslinked insoluble structure, in which case the specification of timing is appropriate. While a transition from a dried state to a hydrated state would results in weight increases and generally some volume increase, changes from an initial state formed in aqueous solution to an aged state may or may not involve an increase in weight or volume over time, and may results in some time windows in decreases.

The hydrogels for intrauterine placement can have moderate swelling with sufficient swelling to facilitate filling the space but not excessive swelling to result in uncomfortable pressure on the patient. In some embodiments, the hydrogel can have a swelling of no more than 300 weight percent, in further embodiments from about 10 wt % to about 200 wt % and in further embodiments form about 20 wt % to about 100 wt %. In alternative embodiments, the hydrogel can experience syneresis, or a shrinking on a weight basis, generally also on a volume basis, following initial formation, which for convenience is referred to as a negative swelling. Thus, overall swelling can be from about −25 wt % to about 300 wt %, in further embodiments from about −15 wt % to 200 wt %, and in other embodiments from about −10 wt % to about 100 wt %. Swelling (positive or negative) can be determined by the weight of polymer with aqueous solution of buffered saline absorbed into the polymer after 24 hours of contact with the aqueous environment relative to the weight of the polymer and absorbed aqueous solution following crosslinking into an insoluble mass, which generally occurs after several seconds. The hydrogel can be biodegradable so that the uterine space clears after a suitable period of time that the healing process does not trade the hydrogel material itself. In some embodiments, the hydrogel is fully biodegraded in from about 1 day to about 29 days, in further embodiments from about 3 days to about 21 days, and in additional embodiments from about 5 days to about 14 days. For certain applications, such as drug delivery, it may be desirable for the hydrogel to biodegrade over a longer time period, for example, a 30 days or longer. Also, the hydrogel can be selected to be soft so as to be gentle on the tissue, yet not so soft as to be extrudable from the uterus, resulting in unpredictable persistence within the cavity. The intrauterine persistence of an installed hydrogel is expected to correlate with the duration of time in which the hydrogel has a modulus above a threshold range, which is estimated to be about 1 kPa to about 10 kPa. The expulsion forces would tend to be patient dependent, so that the time dependent decay of the modulus can be selected to yield values suitable to maintain the hydrogel in the uterine cavity for a majority of patients. Below this estimated range, the hydrogel is expected to have to insufficient resistance to compressive forces to resist being expunged from the uterus. Specifically, the hydrogel can have an initial Young's (elastic) modulus (for convenience evaluated 12 hours after initial gelling) from about 3 kPa to about 300 kPa, in further embodiments from about 5 kPa to about 250 kPa and in additional embodiments from about 5 kPa to about 200 kPa. The modulus is a measure of compressive force per unit area divided by the change in volume per unit volume. A gel plug can be used to make the measurement using an Instron or alternative brand compressive instrument, in which the stress/strain slope is measured over the first 20% of compression. As shown in Example 3, a gel prepared from a pre-mixed precursor formulation showed a higher initial modulus value and a slower rate of modulus decrease as compared to a gel prepared from a separated formulation. This result suggests that the pre-mixed precursor formulations provide advantages over separated formulations for extending persistence in the uterus. The premixed precursor hydrogel systems also provide good dilution resistance during delivery and good space filing properties. These advantages are especially useful in privileged spaces, such as the uterus, where slower diffusion of buffer salts away from the placement site is theorized to contribute to accelerated degradation of the hydrogel. A person of ordinary skill in the art will recognize that additional ranges of swelling, degradation rate and Young's modulus within the explicit ranges above are contemplated and are within the present disclosure.

Suitable crosslinking times vary for different applications. Gelation time can be evaluated in a laboratory setting. In most applications, the crosslinking reaction leading to gelation occurs within about 5 minutes, in some embodiments, within about 1 minutes, in other embodiments in no more than about 30 seconds, in further embodiments from about 1 second to about 20 seconds, and in additional embodiments from about 1.5 seconds to about 15 second, from initiation of delivery to gelation. A person of ordinary skill in the art will recognize that additional ranges of gelation time within the explicit ranges above are contemplated and are within the present disclosure. When delivered into the uterine cavity, gelation evaluation is obfuscated somewhat by delivery of fresh precursors over a time frame spanning the gelation time. The objective generally is to have fast enough gelation to avoid excessive flow out of the cervix and little or no flow into the fallopian tubes, while having a gelatin time slow enough that the cavity uniformly fills and the catheter does not clog. These gelation times do not necessarily correspond with full crosslinking which can occur over a longer time period, but the gelation times correspond with reaching a point of crosslinking in which the hydrogel no longer is flowable, which can be evaluated in vitro under controlled conditions. Crosslinking times can depend on a combination of several factors, including relative concentrations of reactive precursors, the molar ratios of the reactive ends, temperature, and resulting pH after mixing. Gel times may be varied by one or more of altering the pH, temperature, or buffer salt strength of the "accelerator" portion of the in situ system, if present.

Natural polymers, for example proteins or glycosaminoglycans, e.g., collagen, fibrinogen, albumin, and fibrin, may be crosslinked using reactive precursor species with electrophilic functional groups. Natural polymers are proteolytically degraded by proteases present in the body. The precursors may have biologically inert and water soluble cores. When the core is a polymeric region that is water soluble, suitable polymers that may be used include: polyether, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"); poly (vinyl pyrrolidinone) ("PVP"); poly (amino acids); dextran and proteins such as albumin. The polyethers and more particularly poly(oxyalkylenes) or poly(ethylene glycol) or polyethylene glycol can provide desirable properties for the hydrogels.

Synthetic polymers and reactive precursor species may have electrophilic functional groups that are, for example, carbodiimidazole, sulfonyl chloride, chlorocarbonates, n-hydroxysuccinimidyl ester, succinimidyl ester, n-hydroxyl sulphosuccinimidyl esters, sulfosuccinimidyl esters, or mixtures thereof. In some embodiments of particular interest, the electrophylic functional groups comprise N-hydroxy succinimidyl succinate (SS) esters that provide desirable crosslinking rates to form the hydrogel and degradation rates for the hydrogel subsequently in vivo.formed hydrogel. The term synthetic means a molecule that is not found in nature, e.g., polyethylene glycol. The nucleophilic functional groups may be, for example, amine, such as primary amines, hydroxyl, carboxyl, and thiol. Primary amines can be desirable reactants with NHS electrophilic groups. The polymers in embodiments of particular interest have a polyalkylene glycol portion, and can be polyethylene glycol based. The polyethylene glycol based polymer precursors can have a branched core to provide a selected number of arms that provide a plurality of crosslinking functional groups. The polymers generally also have a hydrolytically biodegradable portion or linkage, for example an ester, carbonate, or an enzymatically degradable amide linkage. Several such linkages are well known in the art and originate from alpha-hydroxy acids, their cyclic dimers, or other chemical species used to synthesize biodegradable articles, such as, glycolide, dl-lactide, l-lactide, caprolactone, dioxanone, trimethylene carbonate or a copolymer thereof. In some embodiments, a reactive precursor species can have two to ten nucleophilic functional groups each, and corresponding reactive precursor species can have two to ten electrophilic functional groups each.

In some embodiments, a hydrogel is selected and delivered that at least partially fills a uterus, and in embodiments of particular interest, the hydrogel substantially fills a uterus. Thus, upon fully crosslinking, the hydrogel is shaped like an interior of a uterus. While filling the uterus, a hydrogel can form a coating on at least a portion of an intrauterine tissue. In some embodiments, a hydrogel substantially fills a uterus and has contact with substantially all of the tissues exposed inside the uterus and in the cervical canal. The introduction of fluent precursor(s) or precursor solutions into a uterus that form a hydrogel having a volume that is essentially equal to the volume of the fluent precursor(s) or precursor solutions, with some potential adjustment based on swelling, can contact substantially all of the tissues exposed inside the uterus because a fluid will conform to the shape of the tissues. Nonetheless, it is appreciated by persons of ordinary skill in the art that even substantially complete contact may suffer from imperfections.

In some embodiments, a method is used to form a hydrogel on a tissue until the color of the hydrogel indicates that a predetermined volume of hydrogel has been deposited on the tissue or within the space. The precursors are continually introduced into the space until the color of the materials that enter that space and flow out are deemed to have achieved a suitable content, as indicated by observation of the visualization agent disposed in the materials that flow out. For example, two fluent precursors associated with a blue dye are introduced into a uterus and pumped therein until the color of materials exiting the uterus indicates that unwanted fluids have been washed out of the uterus and the uterus is substantially full of the precursors.

The user may use visualization agents to see the hydrogel with the human eye or with the aid of an imaging device that detects visually observable visualization agents, e.g., a videocamera that is used during operative hysteroscopy. A visually observable visualization agent is an agent that has a color detectable by a human eye. A characteristic of providing imaging to an X-ray or MRI machine is not a characteristic sufficient to establish function as a visually observable visualization agent. An alternative embodiment is a visualization agent that may not normally be seem by the human eye but is detectable at a different wavelength, e.g., the infrared or ultraviolet, when used in combination with a suitable imaging device, e.g., an appropriately equipped videocamera.

The three dimensional hydrogel structure can be resistant to expulsion from the uterine cavity, thus serving to keep the uterine walls apart and prevent the formation of scar bridges, or adhesions. Over time the hydrogels degrade and naturally exit the uterine cavity by either systemic absorption, or mostly as discharge through the cervix and vagina.

In some embodiments, a hydrogel is selected and delivered that at least partially fills a uterus, and in embodiments of particular interest, the hydrogel substantially fills a uterus. Thus, upon fully crosslinking, the hydrogel is shaped like an interior of a uterus. While filling the uterus, a hydrogel can form a coating on at least a portion of an intrauterine tissue. In some embodiments, a hydrogel substantially fills a uterus and has contact with substantially all of the tissues exposed inside the uterus and in the cervical canal. The introduction of fluent precursor(s) or precursor solutions into a uterus that form a hydrogel having a volume that is essentially equal to the volume of the fluent precursor(s) or precursor solutions, with some potential adjustment based on swelling, can contact substantially all of the tissues exposed inside the uterus because a fluid will conform to the shape of the tissues. Nonetheless, it is appreciated by persons of ordinary skill in the art that even substantially complete contact may suffer from imperfections.

Visualization Agents

Where convenient, the biocompatible crosslinked hydrogel polymer may contain visualization agents to improve their visibility during surgical procedures. Visualization agents are especially useful when used in minimally invasive surgery (MIS, e.g., laparoscopy) procedures, due among other reasons to their improved visibility on a color monitor.

Visualization agents may be selected from among any of the various non-toxic colored substances suitable for use in medical implantable medical devices, such as FD&C BLUE dyes 1, 2, 3 and 6, indocyanine green, or colored dyes normally found in synthetic surgical sutures. In some embodiments, green or blue colors are desirable because these have better visibility in presence of blood or on a pink or white tissue background.

The visualization agent may be present with the solution comprising the reactive precursor species, in the accelerator solution or in both. It can be convenient to include a visualization agent with the accelerator solution. The selected colored substance may or may not become chemically bound to the hydrogel. Additional visualization agents may be used, such as fluorescent (e.g., green or yellow fluorescent under visible light) compounds (e.g., fluorescein or eosin), x-ray contrast agents (e.g., iodinated compounds) for visibility under x-ray imaging equipment, ultrasonic contrast agents, or MRI contrast agents (e.g., Gadolinium containing compounds). Visualization agents may also be biologically active agents suspended or dissolved within the hydrogel matrix, or the materials used to encapsulate a biologically active agents, if present.

Further visualization of the hydrogel implant can be achieved directly after instillation using transvaginal ultrasound (TVUS). The presence and extent of hydrogel filling the uterine cavity (comprising the endometrial cavity and sonographically-visible cervical canal) is hyperechoic directly after instillation due to presence of some entrapped air and it will be seen as an echogenic (bright) space where it is filling the uterine cavity.

As noted above, visually observable visualization agents can be advantageously used for some embodiments. Wavelengths of light from about 400 to 750 nm are observable to the human as colors (R. K. Hobbie, Intermediate Physics for Medicine and Biology, $2^{nd}$ Ed., pages 371-373). Blue color is perceived when the eye receives light that is predominantly from about 450 to 500 nm in wavelength and green is perceived at about 500 to 570 nm (Id.). Further, since the eye detects red or green or blue, a combination of these colors may be used to simulate any other color merely by causing the eye to receive the proportion of red, green, and blue that is perceived as the desired color by the human eye. The color blue, as used herein, means the color that is perceived by a normal human eye stimulated by a wavelength of about 450 to 500 nm and the color green, as used herein, means the color that is perceived by a normal human eye stimulated by a wavelength of about 500 to 570 nm.

In some embodiments, the visualization agent is present in the hydrogel system during application into a void such as the uterus through the delivery systems described herein. In such applications, the target tissue of the intrauterine surface is not, or cannot be, visualized. The presence of the visualization agent in application may enable the user to detect when the cavity has been sufficiently filled with material through the presence of excess exiting the target cavity. In the case of an intrauterine application following a surgical intervention, the presence of a blue or green visualization aid allows for differentiation from excess bodily blood and fluids resultant of the surgery, as well as confirmation that the application and hydrogel crosslinking has occurred.

Suitable biocompatible visualization agents are FD&C BLUE #1, FD&C BLUE #2 Indocyanine green. Methylene blue, while providing appropriate potential for visualization, is less desirable due to reports of allergenic potential in gynecological procedures, relative to other medically acceptable colorants and dyes that provide a contrasting color with red serosanguinous fluids. One or both of these agents can be present in the final electrophilic-nucleophilic reactive precursor species mix at a concentration of more than 0.05 mg/ml and in some embodiments in a concentration range of at least 0.1 to about 12 mg/ml, and in further embodiments in the range of 0.1 to 4.0 mg/ml, although greater concentrations may potentially be used, up to the limit of solubility of the visualization agent. These concentration ranges were found to give a color to the hydrogel that was desirable without interfering with crosslinking times (as measured by the time for the reactive precursor species to gel) and were determined to be more radiation stable than other visualization agents such as methylene blue. The visualization agent may also be a fluorescent molecule. The visualization agent is generally not covalently linked to the hydrogel. A person of ordinary skill in the art will recognize that additional ranges of visualization agent concentrations within the explicit ranges above are contemplated and are within the present disclosure.

In some embodiments, a method is used to form a hydrogel on a tissue until the color of the hydrogel indicates that a predetermined volume of hydrogel has been deposited on the tissue or within the space. The precursors are continually introduced into the space until the color of the materials that enter that space and flow out are deemed to have achieved a suitable content, as indicated by observation of the visualization agent disposed in the materials that flow out. For example, two fluent precursors associated with a blue dye are introduced into a uterus and pumped therein until the color of materials exiting the uterus indicates that unwanted fluids have been washed out of the uterus and the uterus is substantially full of the precursors.

Drug Delivery

In many applications, the hydrogel applied in contact with a patient's tissue may contain a biologically active agent. Intrauterine drug delivery pathways offer several potential advantages. First, the uterine and vaginal linings are less prone to localized irritation resulting from depot proximity as compared to buccal or ocular mucosal membranes. Second, the intrauterine enzymatic activity is significantly lower in comparison to a gastrointestinal route. Third, the intrauterine pathway bypasses first-pass metabolic losses found in the oral administration pathway, increasing the bioavailability drugs and potentially lowering the dose required. Also, the uterine cavity provides a cul-de-sac which can be filled, unlike the gastrointestinal tract which has continuous flow. As with any localized delivery device, intrauterine therapeutic targets benefit greatly from improved therapy with reduced systemic effects that typically result from higher dose traditional administration routes. The use of hydrogels formed in situ for drug delivery is described in U.S. Pat. No. 9,125,807 to Sawhney et al., entitled "Adhesive Hydrogels for Ophthalmic Drug Delivery," incorporated herein by reference. The hydrogels can also be enhanced with respect to imaging, as described in U.S. Pat. No. 8,383,161 to Campbell et al., entitled "Radiopaque Covalently Crosslinked Hydrogel Particle Implants," incorporated herein by reference.

Crosslinked hydrogel materials advantageously may be used for localized or systemic drug therapy via intrauterine administration. Biologically active agents or drug compounds that may be added and delivered from the crosslinked polymer or gel include: proteins, glycosaminoglycans, carbohydrates, nucleic acid, inorganic and organic biologically active compounds where specific biologically active agents include but are not limited to: enzymes, anti-infectives, antifungals, anti-inflammatories, antineoplastic agents, local anesthetics, hormones, angiogenic agents, anti-angiogenic agents, growth factors, antibodies, neurotransmitters, psychoactive drugs, anticancer drugs, chemotherapeutic drugs, drugs affecting reproductivity, genes, oligonucleotides or combinations thereof. In some embodiments, the class of therapeutics targets disease states singular to women's health; these may be local conditions within the uterus itself, and/or health conditions capable of treatment via intrauterine transmucosal transport into the systemic circulation, such as hormonal therapy for post-menopausal women.

To prepare such crosslinked composition, the bioactive compounds described above may be mixed with either solution used to make the hydrogel, and the drug can be added into the aqueous solution, prior to making the aqueous solution or during the aseptic manufacturing of the monomers. In additional or alternative embodiments, a bioactive compound can be added to the accelerator solution for incorporation into the hydrogel. In using the crosslinked composition for drug delivery as mentioned above, the amount of crosslinkable polymer, crosslinker and the dosage agent introduced in the host can be selected depending upon the particular drug and the condition to be treated, consistent with not significantly interfering with hydrogel properties In some embodiments, the active agent or agents are present in a separate phase when crosslinker and crosslinkable polymers are reacted to produce a crosslinked hydrogel. This phase separation prevents participation of bioactive substance in the chemical crosslinking reaction such as reaction between the ester group and amine group. The separate phase may also help to modulate the release kinetics of active agent from the crosslinked material or gel, where 'separate phase' could be oil (oil-in water emulsion), biodegradable vehicle, and the like. Biodegradable vehicles in which the active agent may be present include: encapsulation vehicles, such as microparticles, microspheres, microbeads, micropellets, and the like, where the active agent is encapsulated in a bioerodable or biodegradable polymers such as polymers and copolymers of: poly(anhydride), poly(hydroxy acid)s, poly(lactone)s, poly(trimethylene carbonate), poly(glycolic acid), poly(lactic acid), poly(glycolic acid)-co-poly(glycolic acid), poly(orthocarbonate), poly(caprolactone), crosslinked biodegradable hydrogel networks like fibrin glue or fibrin sealant, caging and entrapping molecules, like cyclodextrin, molecular sieves and the like. Microspheres made from polymers and copolymers of poly(lactone)s and poly(hydroxy acid) are particularly suitable as biodegradable encapsulation vehicles. Drug delivery vehicles can further comprise visualization agents.

These biologically active agents may include anti-infectives or anti-fungals for the treatment of uterine infections, where effectivity of the agent is improved due to its local target proximity. For example, the following antimicrobials can be suitable: broad spectrum antibiotics (such as penicillins and cephalosporins), metronidazole (for bacterial vaginosis and trichomonas), fluconazole (anti-fungal-for yeast infection), doxycycline, or azithromycin. Certain cases may call for the anti-infective agent to be deployed prophylactically during high risk procedures or in high risk immunocompromised populations. Anti-inflammatories, such as NSAIDs or steroids, are another class of agents that may be used to treat conditions such as endometriosis, without the systemic side effects associated with long term consumption of these agents. In other embodiments, the application of the hydrogel containing an anti-bacterial or anti-viral as a supplemental barrier to a compromised cervix to prevent preterm birth resulting from infection.

Agents such as hormones benefit from local intrauterine delivery, ranging from treatment of endometriosis, contraception, and as hormone replacement therapy (HRT) in post-menopausal women. Oral contraceptive consumption is associated with increased risks in thromboembolisms as well as rates of breast cancer. More benign side effects of oral contraceptive use, such as mood changes, weight gain, intermenstrual vaginal bleeding and spotting, and loss of libido, may lead to inconsistent oral administration or discontinuation, translating into a failure rate for oral contraceptives as high as 5% during the first year of use. On the other end of the life cycle, oral administration of HRT in post menopausal women is associated with an increased risk for coronary heart disease, stroke, and venous thromboembolism, as well as increased risk for breast cancer the longer the treatment lasts.

Intrauterine devices (IUDs) are mechanical devices capable of delivering hormones slowly and directly to the uterus. Mirena, a commercially approved levonorgestrel-releasing intrauterine system, is approved for delivery and effectiveness lasting up to 5 years. IUDs offer the advantages of prolonged local delivery of progesterone or levonorgestrel via depots built into the arms of the T-shaped device. IUDs have clinically demonstrated lower side effects associated with low systemic uptake of the hormone therapeutics, but still risk irregular bleeding, perforation, and bacterial/fungal colonization as a result of the mechanical nature and design of the device. See, for example, published U.S. patent application 2018/0008536 to Jukarainen et al., entitled "Drug Delivery System Comprising a Non-Steroidal Anti-inflammatory (NSAID) and a Progestogenic Compound and Method for Manufacturing," incorporated herein by reference.

In one embodiment, the application involves delivery of an in situ forming hydrogel with an excess of hormone amounting to 10, 20 30 up to 50% or more suspended in the premixed hydrogel precursor component of the applicator system. Sustained delivery of the hormone would be achieved through the low solubility of these drugs, allowing for extended delivery directly to the uterus for treatment of conditions such as endometriosis. In HRT, the larger hormone doses suitable for contraception or treatment of endometriosis may have adverse side effects even delivered directly to the uterine space. In other embodiments, where delivery control should be precise, low sustained levels of hormone treatment may be obtained through secondary encapsulation of hormone, and suspension of encapsulated agents into the premixed precursor component of the applicator system for delivery. In some embodiments, the secondary encapsulation may use non-erodible materials to achieve even longer therapeutic delivery times; these non-erodible particles would be released, discharged through normal excretions as the hydrogel matrix breaks down and is resorbed.

In other embodiments, the application of a hydrogel to the uterine cavity takes advantage of the dense vascularization of the uterus, primarily the uterine vein, for the delivery of agents systemically. Agents delivered via the uterus bypass the first pass effect, where total oral bioavailability of the drug may be reduced due to absorption into the hepatic portal system and metabolization by the liver, resulting in excessive doses to reach therapeutic effect. For some agents, oral delivery is not an option at all due to complete loss of the drug to first pass effect. In other cases, the oral administration poses side effects associated with repeat dosing.

Bisphosphonates, a class of drug used for the treatment of osteoporosis, is associated with gastrointestinal distress, inflammation, and erosions of the esophagus. In one embodiment, the intrauterine application of a hydrogel containing a suspension of bisphosphonate particles or encapsulated bisphosphonate to deliver systemic therapeutic levels using less drug without the side effects associated with oral administration. In women who are post-menopausal, intrauterine drug depots could be used to deliver drugs over extended periods of several months.

Select Embodiment—Preventing Intrauterine Adhesions

In some embodiments, a method involves preventing adhesion in a uterus, the method comprising introducing a flowable material into a uterus to tamponade a surface of the uterus. The tamponade may be effective to reduce bleeding. The material may be a hydrogel. The material may be a stent. The material may separate at least two opposing portions of the surface to prevent contact between the two opposing portions. The material may substantially fill the uterus. The material may be applied through a flexible catheter with a rounded atraumatic tip. The material may be applied through the catheter delivery system in conjunction with a feature outside the catheter shaft, such as egress limiter, to reduce material run off and reduce material application variability. The material can be delivered with transcervical delivery or laparoscopically. The catheter may be of reduced profile and diameter, ideally less than 5.5 F, for the reduced exit track profile after substantially filling the uterus. The resulting application can be visualized under ultrasound during and post-administration, the degree of separation of the tissues is quantifiable and translatable to improvement in adhesion prevention.

The material may be substantially formed in the uterus. The material can comprise a visualization agent, such as a blue or green colorant. The material may be partially formed outside the uterus and formation of the hydrogel may be completed in the uterus.

A desirable intrauterine anti-adhesive device is easy to use and delivers a hydrogel composition that persists locally during the main phase of adhesion, is re-absorbable and is biocompatible with no interference with the normal tissue repair process. See, Torres-De La Roche L A, Campo R, Devassy R, et al. Adhesions and Anti-Adhesion Systems Highlights. Facts Views Vis Obgyn. 2019; 11:137-149, incorporated herein by reference. The desired system can persist long enough to meet the time window for healing (3-10 days) but not so long that the adhesion barrier itself is encapsulated as part of the healing response. In the case of preventing intrauterine adhesions, injury to the tissue due to incidental contact during the procedure, or from the procedure itself, results in the loss of basement membrane structures, blood-material interactions, provisional matrix formation, cellular necrosis, and inflammatory responses. These events, in turn, may affect the extent or degree of granulation tissue formation, foreign body reaction, and fibrosis or fibrous capsule development. With implants, the process of organization with the development of fibrous tissue leads to the well-known fibrous capsule formation at the tissue/material interface. The ideal persistence of a resorbable adhesion barrier material is two-fold: the material should persist in significant fashion to provide a suitable barrier to adhesion formation, but not persist such time that an adhesion is formed through fibrous encapsulation of the barrier material itself.

EXAMPLES

Example 1: Bench Top Polymer Testing of Pre-Mixed Formulations

This example illustrates the effect of percent solids and precursor composition on the degradation of hydrogel formulations.

A set of hydrogels were formed by crosslinking an electrophilic precursor and a nucleophilic precursor, identified as Precursor A and Precursor B, respectively. Sample 1 of Table 1 was a control sample prepared according to the previous work described in U.S. Pat. No. 7,347,850. Precursor A was dissolved in 0.01 M pH 4.0 sodium phosphate monobasic buffer solution. Precursor B was separately dissolved in 0.1 M sodium borate buffer, pH 9.5 to form an amine precursor/accelerator solution. As noted in Table 1, the delivery mode of the precursor in sample 1 was separated (S). A 1.5 ml aliquot of the Precursor A solution was drawn into a first syringe. A 1.5 ml aliquot of the Precursor B solution was drawn into a second syringe. A Y connector with two luer lock connections was attached to a ¼" tube adaptor to luer lock fitting, and the tube adaptor attached to ¼" ID clear silicone tubing (Silastic®) containing a static mixing element proximal to the Y connector. The first syringe and the second syringe were attached to the Y connector and a plunger cap was added to the ends of the syringes to ensure equal volume deployment from the two syringes. The syringes were deployed, injecting material having a percent solids according to Table 1 into the length of the silicone tubing. Initial gelation was observed to occur within about 0.5 to 5 seconds, as evidenced by air bubble movement within the tubing.

In samples 2-14 of Table 1, the Precursor A and Precursor B were pre-mixed (PM) with an acid buffer and then mixed with a basic accelerator solution to form a hydrogel. For each pre-mixed sample, an ester-amine precursor solution was prepared by mixing Precursor A and Precursor B in a 1:1 ratio of reactive ester end groups of Precursor A to reactive amine end groups of Precursor B and dissolving the mixture in the 0.1% $NaH_2PO_4$ (sodium phosphate monobasic) buffer solution (pH 4) to form a pre-mixed ester-amine precursor solution. A 1.5 ml aliquot of the ester-amine precursor solution was drawn into a first syringe. An accelerator solution (pH approximately 9.8-9.9) was prepared by mixing 0.045 M sodium borate decahydrate and 0.2 M sodium phosphate dibasic. A 1.5 ml aliquot of the accelerator solution was drawn into a second syringe. The above procedure was followed using these two filled syringes. Initial gelation was observed to occur between 3-5 seconds, as evidenced by air bubble movement within the tubing.

Samples were allowed to continue to gel over the course of 5 minutes to ensure full cure. Using a razor blade, the silicone tubing containing each gel was cut into three uniform lengths and two gel samples (approximately 0.2 g) were removed from each length. Gel samples were placed in a physiologically representative phosphate-buffered saline solution (PBS) at 50 C (accelerated) and 37 C (real-time) conditions, then checked at regular intervals until they were no longer visually detectable. The range of disappearance times at 50 C and at 37 C for each set of 3 gel samples is shown in Table 1.

(4A40k PEG SG). Precursor B was an eight armed PEG-based precursor having a 20,000 Da molecular weight and primary amine functional end groups (8A20k PEG NH2). The percent solids was varied from 4% to 7.5%. The disappearance times at 37 C ranged from 16-31 days, with the disappearance times lower for the samples with lower percent solids.

For samples 11-14, Precursor A was an eight armed PEG-based precursor having either a 15,000 Da molecular weight and succinimidyl succinate (SS) functional end groups (8A15k PEG SS). Precursor B was either trilysine acetate. The percent solids was varied from 7.5% to 12%. The disappearance times at 37 C ranged from about 5 days (113 hours) to about 8 days, with the disappearance times lower for the samples with lower percent solids.

Additional gel time studies were conducted using the pre-mixed precursors described in this example. In one study, 0.1 ml of the pre-mixed ester-amine precursor solution was pipetted into a test tube containing a flea stir bar. The test tube was positioned in the center of a heating stir plate and set to 1000 rpm. A 0.1 ml aliquot of an accelerator solution was added to the test tube using a pipettor. Gel time was noted as the time of injection to the time of stopping the stir bar in mid motion. Injectability of the formulations through a catheter was also tested to determine if there was evidence of catheter clogging and an ability to pause the delivery. Gel times of about 2.5 to 2.9 seconds were observed for a pH 10.03 accelerator solution. Gel times of 1.5 to 1.8 seconds were observed for the a pH 10.3 accelerator solution. Blended solutions with an accelerator solution pH 10.03 were delivered via both continuous and intermittent injection (1 second pause) without clogging of the catheter. With the pH 10.3 accelerator solution, gel times as low as 1.5 seconds were observed without clogging of the catheter during continuous delivery. The results showed that

TABLE 1

| Sample | Precursor A | Precursor B | Mode | Solids | Disappearance at 50 C., days | Disappearance at 37 C., days |
|---|---|---|---|---|---|---|
| 1 | 4a20kPEG SG | Trilysine Acetate | S | 9.0% | 11.5 | 41 |
| 2 | 4a20kPEG SG | Trilysine Acetate | PM | 7.5% | 10 | 34-36 |
| 3 | 4a20kPEG SG | Trilysine Acetate | PM | 5.0% | 9 | 31-34 |
| 4 | 4a40kPEG SG | 8A20kPEG NH2 | PM | 7.5% | 9 | 29-31 |
| 5 | 4a40kPEG SG | 8A20kPEG NH2 | PM | 6.0% | 8-8.5 | 27-29 |
| 6 | 4a20kPEG SG | Trilysine Acetate | PM | 4.5% | 6-7 | 20-23 |
| 7 | 4a20kPEG SG | Trilysine Acetate | PM | 4.0% | 6-7 | 20-23 |
| 8 | 4a40kPEG SG | 8A20kPEG NH2 | PM | 5.0% | 4.5-5 | 16-18 |
| 9 | 4a40kPEG SG | 8A20kPEG NH2 | PM | 4.5% | 4.5-5 | 16-18 |
| 10 | 4a40kPEG SG | 8A20kPEG NH2 | PM | 4.0% | 4-4.5 | 16-18 |
| 11 | 8a15kPEG SS | Trilysine Acetate | PM | 12% | 2.25-3 | 7-8 |
| 12 | 8a15kPEG SS | Trilysine Acetate | PM | 11% | 2.2-2.25 | 7-8 |
| 13 | 8a15k PEG SS | Trilysine Acetate | PM | 10% | 1.9-2.6 | 7-8 |
| 14 | 8a15k PEG SS | Trilysine Acetate | PM | 7.5% | 1.0-1.7 | 4.7-6 |

Mode refers to whether the gel was prepared from separated precursor solutions ("S") or a pre-mixed precursor solution and an accelerator solution ("PM").

For samples 1-3, 6, and 7, Precursor A was a four armed PEG-based precursor having a 20,000 Da molecular weight and succinimidyl glutarate (SG) functional end groups (4A20k PEG SG). Precursor B was trilysine acetate. The percent solids was varied from 4 to 9 percent. The disappearance times at 37 C ranged from 20 to 41 days, with the disappearance time generally decreasing with decreasing percent solids.

For samples 4, 5, and 8-10, Precursor A was a four armed PEG-based precursor having a 40,000 Da molecular weight and succinimidyl glutarate (SG) functional end groups the gel time was reduced by increasing the pH of the accelerator solution and that intermittent delivery was enabled by the hydrogel formulations.

This study showed that the pre-mixing of ester and amine precursors can lead to hydrogels which have a desirable range of disappearance times and gel times. The disappearance time was shown to be affected by the percent solids, the ester functional group as well as the molecular weight and composition of each precursor. The disappearance time for the separated formulation was outside of the target range of about 3 to 29 days for in utero use. Disappearance times in the target range were observed for most of the premixed formulations.

Example 2: Swelling Study

This example demonstrates the preparation of hydrogels using pre-mixed precursor solutions and an accelerator. Hydrogel swelling is shown as a function of the pre-mixed precursor solution concentration and as a function of the pot life of the pre-mixed precursor solution.

Two pre-mixed precursor solutions were prepared. A 20% solids precursor solution was prepared by dissolving 1 g of 8-arm 15,000 Da PEG succinimidyl succinate (SS) and a 1:1 functional group equivalent amount of trilysine acetate (approximately 27 mg) in 5 ml of a 20 mM pH 4 $NaH_2PO_4$ (monobasic diphosphate) buffer solution. A 24% solids precursor solution was prepared by dissolving 1 g of 8-arm 15,000 Da PEG succinimidyl succinate (SS) and a 1:1 functional group equivalent amount of trilysine acetate (approximately 27 mg) in 4.2 ml of a pH 4 $NaH_2PO_4$ (monobasic diphosphate) buffer solution.

After a predetermined period of time (the "pot life"), 1.5 ml of the 20% solids precursor solution was drawn into a first syringe. A 1.5 ml aliquot of a pH 9.9 sodium borate/sodium phosphate dibasic accelerator solution, prepared by mixing 0.045M sodium borate decahydrate with 0.2 M sodium phosphate dibasic, was drawn into a second syringe. A Y connector with two luer lock connections was attached to a ¼" tube adaptor to luer lock fitting, and the tube adaptor attached to ¼" ID clear silicone tubing (Silastic®) containing a static mixing element proximal to the Y connector. The first and second syringe were attached to the Y connector and a plunger cap added to the ends of the syringes to ensure equal volume deployment from the two syringes. The syringes were deployed, injecting material into the length of the silicone tubing. Initial gelation was observed to occur between 3-5 seconds, as evidenced by air bubble movement within the tubing. Samples were allowed to continue to gel over the course of 5 minutes. A "10% solids" gel. based on precursor concentrations, was formed. For another sample, the above procedure was modified by first drawing the 24% solids precursor solution into the first syringe and a "12% solids" gel was formed.

Using a razor blade, the silicone tubing containing each gel was cut into three uniform lengths and a gel samples (approximately 0.2 g) was removed from each length. Gel samples were weighed to provide an initial "Weight In," then placed in a physiologically representative phosphate-buffered saline solution (PBS) at 37 C. At 24 hours, samples were carefully removed, blotted dry to remove excess fluid, and reweighed to provide a "Weight Out." Swelling was determined via the following equation:

$$\% \text{ Swell} = \frac{\text{Weight Out} - \text{Weight In}}{\text{Weight In}} \times 100\%$$

Figure 11:
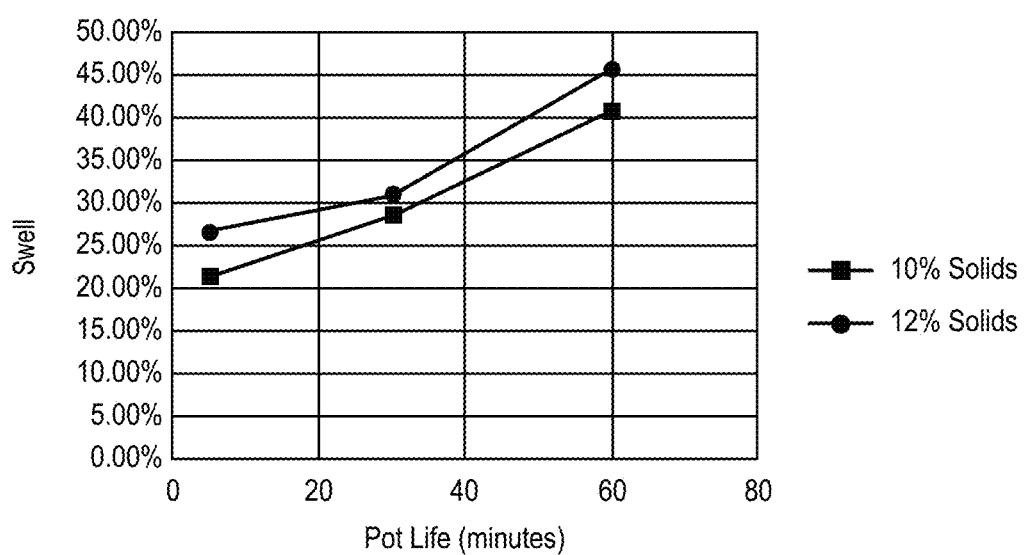
FIG. 11 shows a plot of the swelling of a hydrogel as a function of the pot life in minutes for two pre-mixed formulations.
Figure 12:
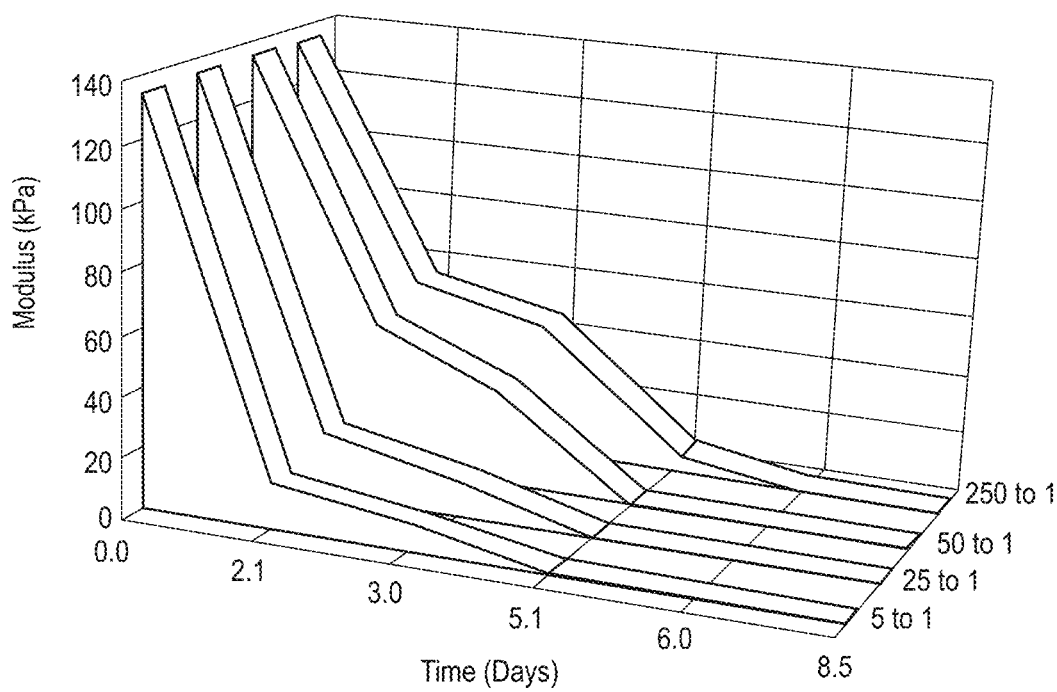
FIG. 12 shows a set of plots of the modulus as a function of time for gel samples formed from various hydrogel systems and tested at 5:1, 25:1, 50:1, and 250:1 dilution ratios.
Figure 13:
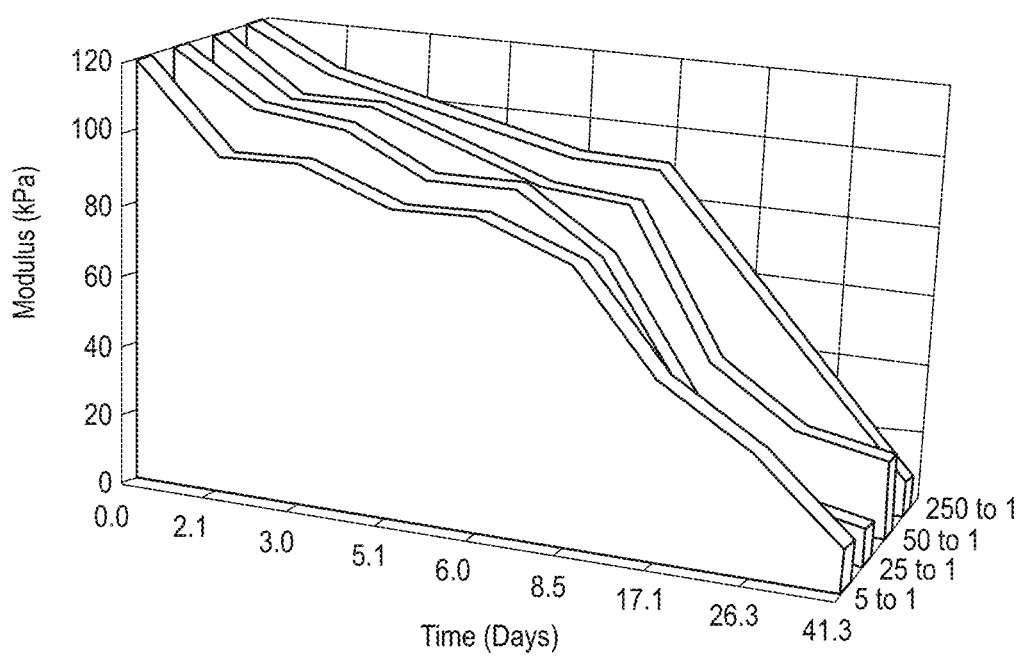
FIG. 13 shows a set of plots of the modulus as a function of time for gel samples formed from various hydrogel systems and tested at 5:1, 25:1, 50:1, and 250:1 dilution ratios.

Hydrogel samples were prepared with three pot life times: 5 minutes, 30 minutes, and 60 minutes. FIG. 11 shows a plot of the swelling of each hydrogel as a function of the pot life in minutes. It is observed that the percent swelling increased with an increase in the percent solids in the pre-mixed precursor solution. Swelling of the hydrogel also increased with pot life time. The 24-hour swelling of the hydrogels was in a range from about 21 wt % to about 46 wt %.

Example 3: Bench Top Polymer Modulus Testing

This example studies the effect of precursor composition and pre-mixing on the modulus of the hydrogel over time.

A set of hydrogels were formed by crosslinking an electrophilic precursor and a nucleophilic precursor, identified as Precursor A and Precursor B, respectively. Four precursor formulations were studied as shown in Table 2. Formulations 1-3 were used to prepare hydrogels by pre-mixing Precursor A and Precursor B in an acidic buffer. Formulation 4 is a comparative formulation in which a hydrogel was formed with separate Precursor A and Precursor B solutions.

For formulations 1-3, an ester-amine precursor solution was prepared according to Table 2 by mixing Precursor A and Precursor B in a 1:1 equimolar ratio of reactive ester end groups of Precursor A to reactive amine end groups of Precursor B and dissolving the mixture in the 0.1% $NaH_2PO_4$ (sodium phosphate monobasic) buffer solution (pH 4). An 1.5 ml aliquot of the ester-amine precursor solution was drawn into a first syringe. An accelerator solution (pH approximately 9.8-9.9) was prepared by mixing sodium borate decahydrate and sodium phosphate dibasic according the weight percentages shown in Table 2. A 1.5 ml aliquot of the accelerator solution was drawn into a second syringe. A Y connector with two luer lock connections was attached to a ¼" tube adaptor to luer lock fitting, and the tube adaptor attached to ¼" ID clear silicone tubing (Silastic®) containing a static mixing element proximal to the Y connector. The first syringe and the second syringe were attached to the Y connector and a plunger cap was added to the ends of the syringes to ensure equal volume deployment from the two syringes. The syringes were deployed, injecting material into the length of the silicone tubing. Initial gelation was observed to occur between 3-5 seconds, as evidenced by air bubble movement within the tubing. Samples were allowed to continue to gel for a period of time that was more than 20 times the initial gelation time (greater than 2.5 minutes) to ensure full cure.

For formulation 4, Precursor A (4a20k PEG SG) was dissolved in the 0.1% sodium phosphate monobasic buffer solution, pH 4, to form an ester precursor solution. A 1.5 ml aliquot of the ester precursor solution was drawn into a first syringe. Independently, Precursor B (trilysine acetate, abbreviated TLA) was dissolved in the 1.2% sodium borate decahydrate buffer, pH 10.3 to form an amine precursor/accelerator solution. A 1.5 ml aliquot of the amine precursor/accelerator solution was drawn into a second syringe. The above procedure was followed using these two filled syringes.

Formulations 3 and 4 are similar in formulation components, however the hydrogel samples were prepared by mixing the components differently. Formulation 3 was used to make a pre-mixed precursor composition with an acidic pH (pH 4) which was reacted with a basic accelerator solution (pH 9.9). Formulation 4 was used to make an acidic ester precursor solution (pH 4) and a basic amine solution (pH 10.3), which were then mixed. Therefore, a comparison of formulations 3 and 4 shows an effect on pre-mixing of precursors versus non pre-mixing of precursors. The comparison also shows the effect of the higher concentration of salts required to achieve the pH 10.3 basic amine solution required to enable the crosslinking of the ester and the amine upon mixing.

TABLE 2

| Formulation | Precursor A | Precursor B | Percent Solids | Sodium borate decahydrate solution | Sodium phosphate dibasic | Sodium phosphate monobasic solution |
|---|---|---|---|---|---|---|
| 1 | 8a15k PEG SS (9.4 wt %) | TLA (0.6 wt %) | 10.0% | 0.8 wt % | 1.4 wt % | 0.1 wt % |
| 2 | 8a15k PEG SG (7.1 wt %) | TLA (0.5 wt %) | 7.6% | 0.7 wt % | 1.3 wt % | 0.1 wt % |
| 3 | 4a20k PEG SG (8.8 wt %) | TLA (0.2 wt %) | 9.0% | 0.8 wt % | 1.4 wt % | 0.1 wt % |
| 4 | 4a20k PEG SG (8.5 wt %) | TLA (0.2 wt %) | 8.7% | 1.2 wt % | — | 0.1 wt % |

Using a razor blade, the silicone tubing containing each gel was cut into three uniform lengths and gel samples (approximately 0.2 g) were removed from each length. Gel samples were placed in a simulated uterine fluid (SUF) having a selected volume corresponding with a target dilution ratio. The term dilution ratio is the ratio of the mass of the SUF to the gel sample mass. The dilution ratio was altered to simulate different constrained volume scenarios. For example, testing the disappearance of the 0.2 g gel sample in 50 g of SUF provides a 250:1 dilution ratio (50 g SUF:0.2 g gel). Disappearance of the formed gels in dilution ratios of 5:1, 25:1, and 50:1, and 250:1 were tested. The lower dilution ratios were used as a way to model in vivo locations with constrained volumes to determine if different diffusion rates of the buffer salts from the gel or a different response to total buffering was observed. It is hypothesized that the gel samples disappear faster in the lower dilution ratio media due to a reduced diffusion of buffer salts from the gel and a resulting extended period of elevated pH. The elevated pH is thought to cause more rapid hydrolysis of the ester functional groups participating in the cross-linking with the amine functional groups, leading to earlier degradation and earlier visual disappearance of the gel sample. The components of SUF are shown in comparison to phosphate-buffered saline solution (PBS) in Table 3. The pH of SUF at 50 C was measured as 7.24. The pH of PBS at 50 C was measured as 7.57.

TABLE 3

| Component | PBS (g/l) | SUF (g/l) |
|---|---|---|
| NaCl | 10 | 4.97 |
| KCl | 0.250 | 0.224 |
| $Na_2HPO_4$ | 1.8 | 0.072 |
| $KH_2PO_4$ | 0.245 | N/A |
| $NaHCO_3$ | N/A | 0.25 |
| $CaCl_2$ | N/A | 0.167 |
| Glucose | N/A | 0.5 |

The modulus of each gel sample was measured as a function of time at 50 C and 37 C (real-time) conditions in each dilution ratio of SUF. Modulus was able to be measured in the range of 5 kPa to 200 kPa. The gel samples were also checked at regular intervals until they were no longer visually detectable. Each gel sample was also tested in a 250:1 dilution ratio of PBS.

FIGS. 12-15 show the modulus as a function of time and dilution ratio at 37 C for gel samples prepared from formulations 1-4. Note that the time axis is not linear. Each of the gel samples showed an initial steep decrease in modulus over a period of about 2 days. The rate of the initial decrease of the modulus and the percent decrease of modulus varied with the dilution ratio. The time to reach the lower modulus limit (5 kPa) was also dependent on the dilution ratio. In general, a decrease in the dilution ratio was correlated with a lower modulus at a given time.

The comparative formulation (formulation 4, FIG. 15) showed a steep decrease in modulus for the 5:1 dilution ratio gel sample. The modulus decreased from 70 kPa at the time of formation of the gel to effectively zero after about 2 days. In contrast, the pre-mixed formulations in a 5:1 dilution ratio showed an initial decrease of about 2 days followed by an extended region or regions of slower decrease in modulus. Formulations 1 and 3 reached an effectively zero modulus at about 5 days. Formulation 2 showed a modulus above about 10 kPa at 41 days. These results show that the modulus profile depends on the ester precursor and percent solids of the pre-mixed formulations.

Figure 14:
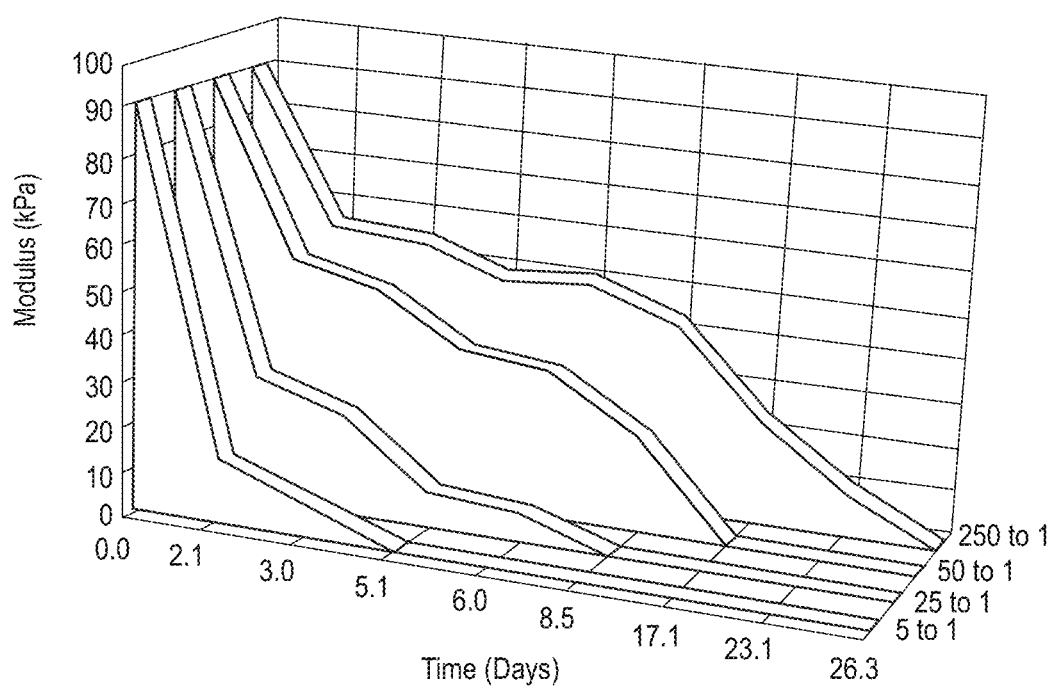
FIG. 14 shows a set of plots of the modulus as a function of time for gel samples formed from various hydrogel systems and tested at 5:1, 25:1, 50:1, and 250:1 dilution ratios.
Figure 15:
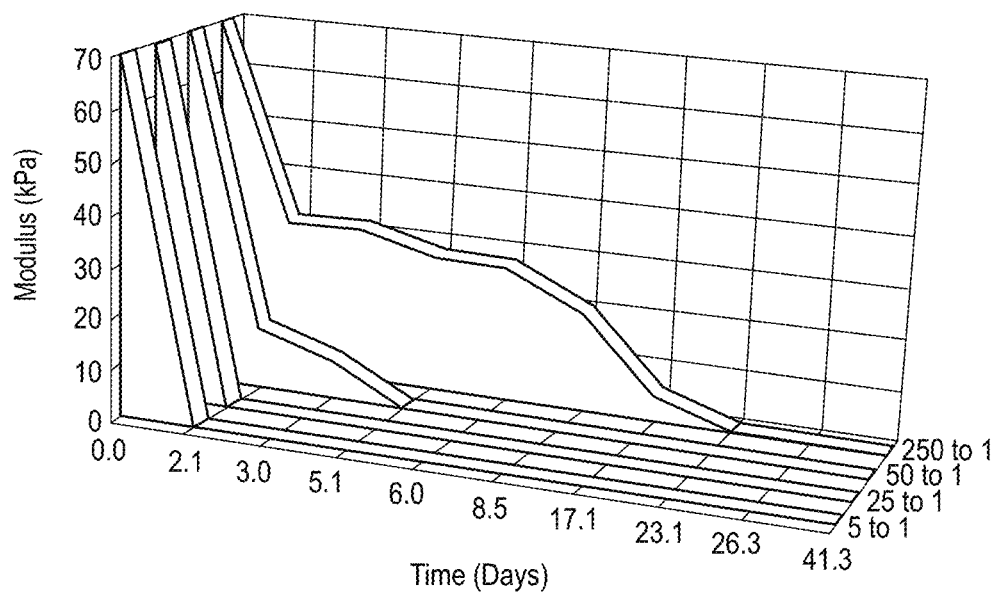
FIG. 15 shows a set of plots of the modulus as a function of time for gel samples formed from various hydrogel systems and tested at 5:1, 25:1, 50:1, and 250:1 dilution ratios.

A comparison of FIGS. 14 and 15 (corresponding to formulations 3 and 4) show that pre-mixing of the precursors can lead to a hydrogel with markedly different modulus properties. The hydrogel formed from the pre-mixed precursors (formulation 3) reached an effectively zero modulus in a 5:1 dilution ratio at about 5 days versus 2 days for formulation 4, extending the time period by about 250%. At each of the dilution ratios, the gel samples from the pre-mixed precursors retained modulus notably longer than the gel samples from the separated precursors. This result suggests that accelerated hydrolysis (or "self-hydrolysis") was occurring in the gel samples from the separated precursors (formulation 4) due to the higher pH required to initiate the cross-linking reaction and that this issue was alleviated via the pre-mixed delivery of the precursors (formulation 3). Avoidance of self-hydrolysis leads to the hydrogel being stiff enough to resist being expunged from the uterus for a longer period of time.

Figure 16:
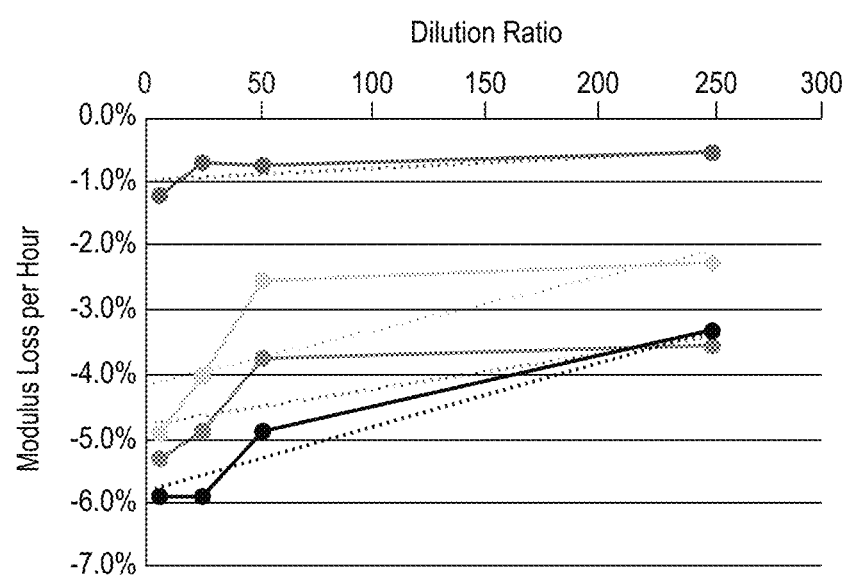
FIG. 16 shows a plot of the modulus loss per hour as function of dilution ratio for three gel samples formed from pre-mixed formulations and a fourth gel sample formed from a separated formulation.

FIG. 16 shows a plot of the percent modulus loss per hour as a function of the dilution ratio for gel samples from each formulation, from top to bottom, formulation 2, formulation 3, formulation 1, formulation 4. Modulus loss rate for the gels from pre-mixed formulations 1-3 were less sensitive to a reduction in the dilution ratio from 250:1 to 50:1 than the gels from formulation 4.

Figure 17:
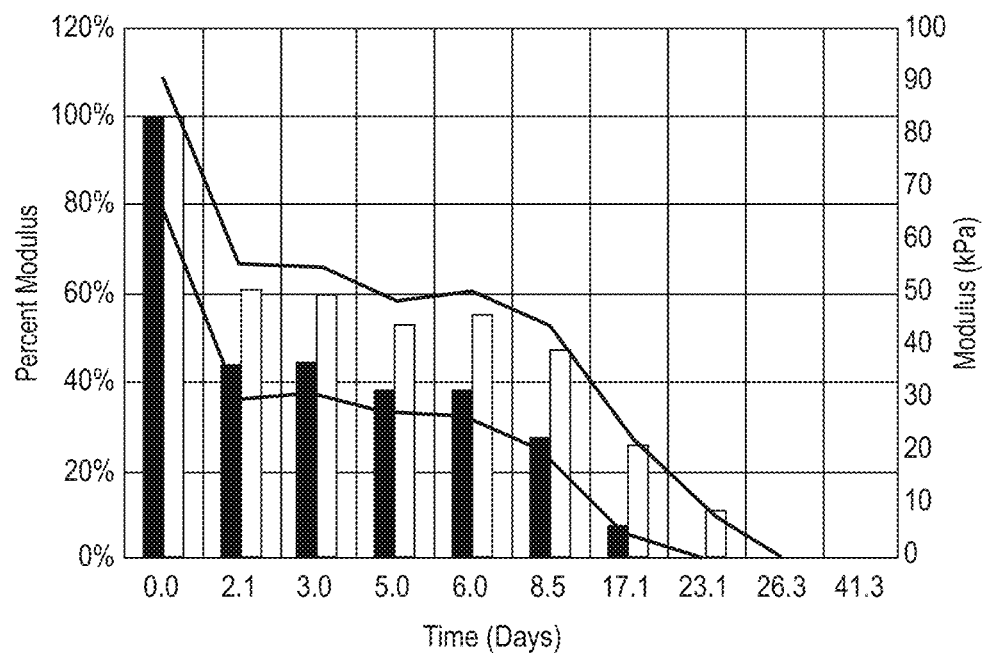
FIG. 17 shows a plot of the percent modulus and the absolute modulus as a function of time in a 250:1 dilution ratio media for a pre-mixed formulation and a separated formulation.

A comparison of the modulus as a function of time for gel samples from formulations 3 and 4 at a dilution ratio of 250:1 is shown in FIG. 17. The bars show the absolute modulus in kPa of each gel as a function of time while the curves show the percent modulus of each gel as a function of time. The data was collected at 50 C to accelerate the experiment, with the presented times being adjusted times from accelerated correlation to 37 C. The gel sample from formulation 3 had an initial modulus of 91 kPa which linearly decreased to 56 kPa (or 62% of the original modulus) over 2.1 days. The gel sample from formulation 4 had an initial modulus of 70 kPa which linearly decreased to 30.5 kPa (or 44% of the original modulus) over 2.1 days. The rate of decrease of the modulus was 18% per day for the pre-mixed formulation versus 27% per day for the separated formulation. Thus the pre-mixed formulation showed a higher initial modulus and a sharper initial decrease in modulus as compared to the separated formulation. At longer times, the decrease in the modulus for the separated formulation was generally more pronounced for the separated formulation than for the pre-mixed formulation. It was observed that at a modulus of approximately 5-10 kPa, the tubular-shaped gel samples had lost the mechanical strength required to stand. It is expected that a hydrogel installed in the uterus would be subject to being expunged once the modulus drops below about 1-10 kPa, with the persistence in the uterus decreasing with decreasing modulus thereafter. The pre-mixed formulation retained a modulus of greater than 10 kPa until about 23 days, while the separated formulation decreased below 10 kPa at about 14 days and remained in the range of about 1 kPa to less than 10 kPa from 14-17 days. Table 4 summarizes the time to the modulus falling below 10 kPa and the time to total visual disappearance of the gels for the four dilution ratios used. In each dilution ratio media, the pre-mixed formulation retained the threshold modulus for a longer period of time. However, the days to disappearance of the gel was lower for the pre-mixed formulation than the separated formulation in each dilution ratio media. In each case, the modulus threshold was reached before total disappearance of the gel. It was also observed that the gap between the time to modulus <10 kPa and the visual disappearance increased with dilution ratio. It is hypothesized that the pH of the formulation may drive the separated formulation to an earlier modulus loss.

TABLE 4

| Dilution Ratio | Formulation 3 Pre-mixed | | Formulation 4 Separated | |
| --- | --- | --- | --- | --- |
| | Days to Modulus <10 kPa | Days to Disappearance | Days to Modulus <10 kPa | Days to Disappearance |
| 5:1 | 3 | 5 | 2 | 2 |
| 25:1 | 5 | 17 | 2 | 2 |
| 50:1 | 8.5 | 23 | 3 | 8.5 |
| 250:1 | 23 | >30 | 14 | >30 |

The results show higher initial modulus and improved retention of modulus for the pre-mixed formulations as compared to the separated formulation. The results also show that constrained volume influences gel persistence and modulus over time. The results suggest that pre-mixed formulations would be more suitable for use in privileged areas of use, such as the uterus, than separated formulations since persistence in the uterus has been shown to be correlated to the gel having enough stiffness to resist being ejected from the uterus. The intrauterine persistence of installed hydrogel formulations is expected to correlate with the time to the modulus falling below about 10 kPa for dilution ratios between about 50:1 and 250:1. This feature of persistence in the uterus was further investigated in vivo in Examples 7 and 8.

Example 4: Swelling Testing in Simulated Uterine Fluid

This example studies the swelling of a pre-mixed formulation from Example 3.

Gels samples were prepared according to Example 3 using formulation 3. The swelling of the gels followed the method of Example 2, with the exception that a 250:1 dilution ratio media SUF was used instead of PBS. Table 5 shows the raw and calculated results.

TABLE 5

| Kit | Sample | Weight In, g | Weight Out, g | Swell Percent |
| --- | --- | --- | --- | --- |
| 1 | 1 | 0.2055 | 0.3611 | 75.72% |
| | 2 | 0.2079 | 0.3644 | 75.28% |
| | 3 | 0.2139 | 0.3685 | 72.28% |
| 2 | 1 | 0.2102 | 0.3447 | 63.99% |
| | 2 | 0.2143 | 0.3795 | 77.09% |
| | 3 | 0.2176 | 0.3793 | 74.31% |

The results show that this pre-mixed formulation resulted in swelling between about 64% and 77% after 24 hours. In comparison, typical swelling for a gel formed from the separated formulation 4 of Example 3 was about 110-120% after 24 hours.

Example 5: Bench Top Model Fill Testing

This example illustrates the effect of the percent solids of a hydrogel system on the fill performance.

A set of uterine fill models were prepared from a bi-layer of plastic sheet which was heat molded together along the edges of a triangular shape to form an enclosed triangular cavity having a base of about 7 cm and a height of about 10 cm. The vertex of the triangular cavity was cut away to provide an opening into the cavity. The cavity was provided with saline to simulate residual liquid inside the uterus. Two hydrogel precursor samples were tested: formulation 4 of example 3 (sample 1) and formulation 4 of example 3, diluted 50% with saline (sample 2). As prepared, hydrogel precursor sample 2 had a percent solids of approximately 4.4%. Sample 1 had a percent solids of about 8.7%, as shown in Table 2. The saline was colorless while the hydrogel precursor samples as delivered were blue.

Using an applicator as shown in FIG. 1, the catheter 108 was inserted into the cavity opening until the flow limiter 106 was firmly pressed against the cavity opening. The syringes were prepared according to Example 3. Each sample was injected into the cavity, while continuing to hold the flow limiter 106 firmly against the opening of the cavity. Upon installation of hydrogel precursor sample 2 into the cavity, the majority of the hydrogel leaked past egress limiter 106 as a viscous liquid, as a result the cavity was only partially filled with the soft, viscous hydrogel. Sample 1 showed effective installation of the hydrogel. It was observed that the gel pushed out the (colorless) residual liquids during the filling process. For the lower solids content sample (sample 2), the results indicate that the residual fluid in the cavity caused a dilution that precluded formation of a solid hydrogel that persisted in the cavity. However, for the higher solids content sample, it was observed that the hydrogel was more dilution resistant and was able to evacuate the residual fluids during the filling process. Additional studies were performed in which the amount of headspace in the syringes was varied. It was observed that increasing the headspace resulted a hydrogel with trapped microbubbles. This result suggests that the contrast of the hydrogels when imaged with ultrasound was due in part to the presence of microbubbles in the hydrogels.

This example shows that the percent solids of a hydrogel precursor formulation affects dilution resistance due to residual fluids and overall fill performance. The results indicated that there was a lower limit to the range of percent solids for which a hydrogel system would form a persistent solid hydrogel in utero for a given hydrogel system.

Example 6: Ex-vivo Uterus Benchtop Study

This example illustrates the use of the hydrogel system to delivery hydrogel into an excised human uterus.

In this example, an post-hysterectomy human uterus was obtained according to standard medical research protocols. The weight of the ex-vivo uterus was 101 grams.

A delivery system was assembled according to the image in FIG. 1. Each syringe had a volume of 10 ml. An ester-amine precursor solution was prepared by mixing 8a15K PEG SS and trilysine acetate in a 1:1 ratio of reactive amines to reactive ester end groups and dissolving the mixture in a 20 mM sodium phosphate monobasic buffer solution (pH 4). A 5 ml aliquot of the ester-amine precursor solution was drawn into the first syringe. Into the second syringe, 5 ml of a pH 9.9 sodium borate/sodium phosphate dibasic accelerator solution was drawn. In each case, the first solutions were colored with a dilute concentration of FD&C blue #1. The second solutions were uncolored.

A uterine sound (Integra LifeSciences, product number 30-6000) was used to determine the fundal depth of the ex-vivo uterus. Then the uterine sound was placed along the assembly of catheter 108 and egress limiter 106. The position of the cap element of the egress limiter was adjusted along the catheter using the uterine sound as a guide to provide an approximately 1 cm spacing between distal end of installation tip 102 and the fundus during the installation of the hydrogel. The catheter and egress limiter were connected to the Y-connector and syringe assembly via a luer fitting. The catheter was inserted into the uterus until the distal portion of the cap element entered the cervical canal and the proximal portion of the cap element was pressed against the external orifice of the cervix. A forceps was used to grasp the lip of the cervix to provide resistance during the insertion process. The system was held by syringe holder 118 and firm pressure between the cervix and the cap element was applied while the plunger was pressed to fully deploy the hydrogel system from the syringes. Next, the catheter was pulled out from the uterus, leaving the egress limiter against the external orifice of the cervix. After approximately 2 seconds, the egress limiter was grasped by support sheath 103 and cap element 109 was pulled away from the cervix. The uterus was again weighed. The increase in weight of the uterus after the installation of the installed hydrogel was 10 grams. The majority of the hydrogel precursor remained in the uterus after delivery with a relatively small amount of the precursor forming a surface coating of gel at the external orifice of the cervix. There was no evidence of the installed hydrogel being expelled from the uterus.

Immediately following, the uterus was sectioned along the sagittal plane. A continuous hydrogel was observed that completely filled the uterine cavity including the cervical canal. The solid hydrogel was removed, and it was noted that it held its shape after removal. The uterus was further evaluated by cutting into the fallopian tubes to check for hydrogel. There was no hydrogel found in the fallopian tubes. The results of this study showed that the hydrogel system was effective at delivering hydrogel to a human uterus to form a hydrogel which fully filled the uterine cavity and was firm enough to separate and tamponade the uterine walls and not be ejected at the end of the installation procedure. Furthermore, the hydrogel did not enter into the fallopian tubes.

Example 7: Human Peri-Hysterectomy Study

This example illustrates the use of the hydrogel system to delivery hydrogel into an in-situ human uterus.

Six human patients were part of this study. For each patient, a modified Cook® Goldstein Sonohysterography Catheter was used. The Cook Goldstein Sonohysterography Catheter has a movable acorn-shaped positioner that can be positioned along the catheter, with ink bands located on the catheter as reference marks. The catheter was connected via a luer lock to a dual syringe assembly as described below. In this study, the Cook Goldstein Sonohysterography Catheter was modified by cutting off the catheter at a location proximal to both the round closed tip and the oval sideport. As modified, the catheter had an open port at the distal tip.

Patient selection was based first on a determination that a hysterectomy was medically needed for the patient and second on the willingness of the patient to participate in the experimental study. Prior to enrolment in the study, a diagnostic hysteroscopy and ultrasonography was be performed and video recorded to assess endometrial thickness, the cervical canal length, uterine cavity length and width, and both ostia to assure that the subject has no pathology that would make them ineligible for the study.

For each patient, the first syringe was filled with a first solution containing a mixture of 18% (w/v) of an 8a15K PEG SS precursor and an amount of a trilysine acetate precursor to provide a 1:1 ratio of ester and amine end groups in a 20 mM sodium phosphate monobasic buffer solution (pH 4). The second syringe was filled with a sodium borate/sodium phosphate dibasic accelerator solution, pH 9.8. The first precursor solution contained a dilute concentration of methylene blue. The second precursor solution was uncolored. The syringes were attached to a mixing Y connector via luer lock connections. A plunger cap was added to the ends of the syringes to ensure equal deployment of the two syringes. The Y connector was connected via a third luer lock connection to a 21 gauge tube adaptor. The tube adaptor was attached to 21 gauge catheter made of clear polyethylene tubing. The acorn was adjusted along the catheter length based on the anatomy of each patient such that the tip of the catheter would be positioned at a selected location within the cavity of the body of the uterus during the insertion step.

Following the hysteroscopy and ultrasonography, the modified Cook Goldstein Sonohysterography Catheter was used to deliver the hydrogel system into the uterus. The catheter of the delivery system was inserted into the cervix through the vagina until the resistance and visible catheter length indicated that the acorn was positioned against the external orifice of the cervix. Once positioned, the plunger cap was pressed to inject a 10 ml quantity of fluid from the syringes into the catheter and then into the uterine cavity. A finger of the surgeon was used to control the acorn. The amount of force applied by the surgeon to the acorn was used to regulate the amount of fluid exiting the cervix during installation. After injection, the catheter with attached acorn was removed from the patient. After a period of several seconds of manual pressure on the acorn, the acorn was removed from the patient with a ring forceps. For all of the procedures, it was observed that the catheter tip did not clog during the delivery.

Figure 18:
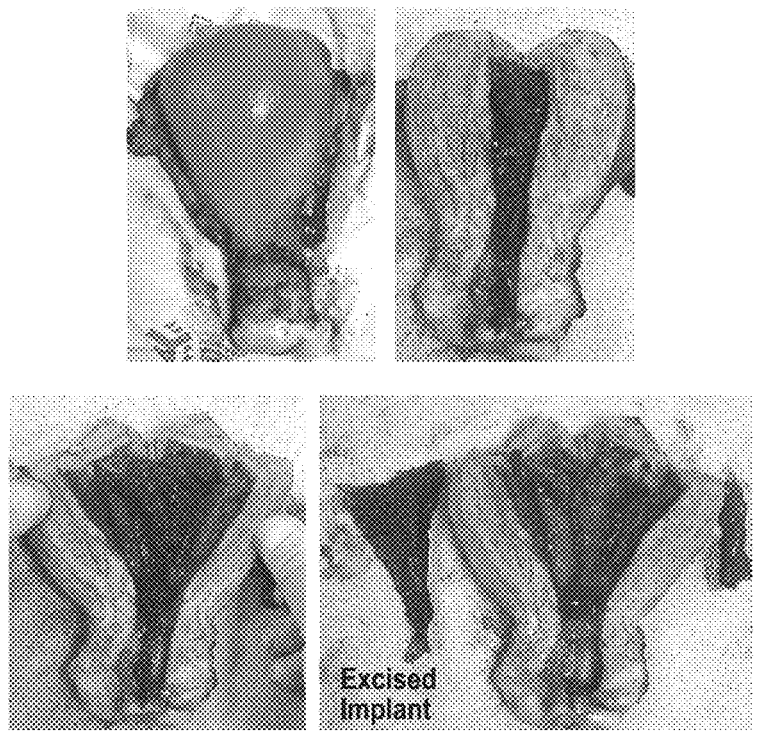
FIG. 18 is a series of post peri-hysterectomy pathology photographs taken after using an applicator to install a hydrogel polymer composition after a uterine ablation procedure. The photographs show a removed uterus, the removed uterus that has been cut open to reveal the installed hydrogel polymer composition, and the cut open uterus with the excised hydrogel implant.

The hysterectomy was then performed to usual standard of care using a surgical method to remove the entire intact uterus. There was no expulsion of the hydrogel during the hysterectomy procedure. The extirpated uterus was sectioned and evaluated for the presence and distribution of the hydrogel implant. All peri-hysterectomy procedures demonstrated fully formed hydrogel implants. For each patient, it was observed that the intrauterine implant coverage was complete within the body of the uterus and that there was no gel in the fallopian tubes. FIG. 18 shows a series of pathology pictures from one patient: top left, a removed uterus; top right and bottom left, the removed uterus that has been cut open to reveal the installed hydrogel; bottom right, the cut open uterus with the excised implant. It can be seen that the gel coats the uterine cavity, and the excised implant is a continuous, solid hydrogel that has the shape of the uterine cavity. The excised hydrogel implants were approximately 1 cm in thickness.

The results of this study demonstrate that the hydrogel system can fill an in-vivo uterus with a persistent hydrogel. The results show that the hydrogels gelled in seconds to form hydrogels that filled the uterus and the cervix even in the presence of normal fluids within the uterus.

Example 8: In-vivo Persistence Study

This example illustrates the use of the hydrogel system to deliver a persistent hydrogel into an in-vivo human uterus.

For this feasibility study, ten female patients were chosen. Patient selection was based first on a determination that an endometrial ablation was medically needed for the patient and second on the willingness of the patient to participate in the experimental study. Prior to enrolment in the study, a diagnostic hysteroscopy and ultrasonography was be performed and video recorded to assess endometrial thickness, the cervical canal length, uterine cavity length and width, and both ostia to assure that the subject has no pathology that would make them ineligible for the study.

The same procedure as outlined in Example 6 was followed except for the modification that the uterus of each patient remained in place (in-situ).

Figure 19:
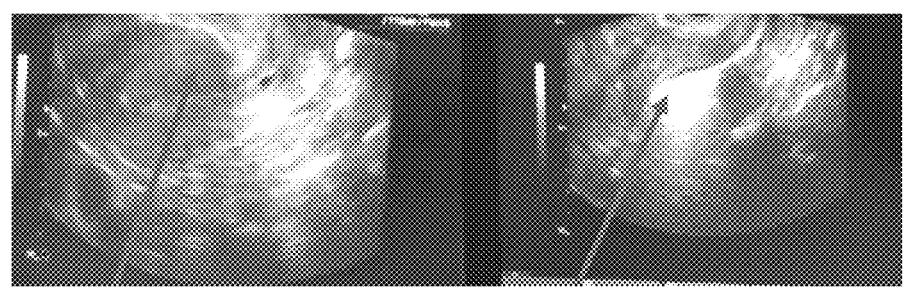
FIG. 19 shows ultrasound images of the uterine cavity for one patient prior to an ablation procedure (left image) and after the ablation procedure and transcervical installation of a hydrogel polymer composition (right image). The arrows show the location of the uterine cavity and the in-situ formed hydrogel which fills and tamponades the uterine cavity.

Immediately after installation of the hydrogel, ultrasound imaging of the uterus was again performed. FIG. 19 shows ultrasound images for one patient prior to the ablation procedure (left image) and after installation of the hydrogel (right image). FIG. 19 indicates with arrows the location of the uterine cavity. The previously empty uterine cavity can be seen to have been filled by the hydrogel implant.

For each patient, intrauterine implant coverage was determined to be complete with no evidence of gel in the fallopian tubes.

Further Disclosure

This further disclosure is directed to various embodiments of the invention.
1. A hydrogel delivery system suitable for intrauterine delivery comprising:
   a first solution;
   a second solution; and
   an applicator comprising a catheter configured for transcervical intrauterine placement with a cap element on the catheter to allow for stopping egress of hydrogel from the cervix, a first reservoir holding the first solution, a second reservoir holding the second solution, a mixer configured for receiving the first solution and the second solution and vigorously mixing the first solution and the second solution to form a blended precursor solution for delivery to the catheter from the mixer, the blended precursor solution having 5 weight percent (wt %) to 12 wt % solids,
   wherein the blended precursor solution gels in no more than about 30 seconds and after 12 hours forms a product hydrogel with an initial Young's modulus greater than 1 kPa, and wherein the product hydrogel persists in a uterine environment for 3 to 29 days.
2. The hydrogel delivery system of 1 wherein the blended precursor solution gels in from about 1 to about 5 seconds.
3. The hydrogel delivery system of 1 wherein the initial Young's modulus is from about 20 kPa to about 150 kPa.
4. The hydrogel delivery system of 1 wherein the product hydrogel after 14 days in a uterine environment has a Young's modulus that is greater than about 10% of the initial Young's modulus.
5. The hydrogel delivery system of 1 wherein the product hydrogel persists in a uterine environment for 3 to 14 days.
6. The hydrogel delivery system of 1 wherein in a time of up to 24 hours after forming the product hydrogel swells by no more than 125%.
7. The hydrogel delivery system of 1 wherein a radiopaque agent is covalently attached to the product hydrogel.
8. The hydrogel delivery system of 1 wherein the product hydrogel is visible under ultrasound.
9. A method for delivering an intrauterine hydrogel, the method comprising:
   combining a first solution and a second solution to form a blended solution, wherein the first solution comprises an aqueous solvent, a first precursor having a hydrophilic core and succinimidyl ester functional group, and a second precursor having a plurality of amine functional groups, and wherein the second solution comprises a buffer solution having a pH greater than 8.2; and
   directing the blended solution into a transcervical positioned catheter to deliver the blended solution into a uterus, wherein the blended solution undergoes covalent crosslinking to gel in no more than about 30 seconds, wherein the catheter has a cap element that can be used to prevent egress of the blended solution to provide pressure to the gelling hydrogel creating distended fill.
10. The method of 9 wherein the uterus comprises residual fluids and wherein the residual fluids have a volume equal to or less than the volume of the blended solution.
11. The method of 10 further comprising removing residual fluids with the positioned catheter prior to the directing.
12. The method of 10 wherein residual fluids exit and the blended solution forms a hydrogel in-situ to effectively fill the uterine cavity.
13. The method of 12 wherein the hydrogel persists in the uterus for 3 to 29 days.
14. The method of 9 wherein a first syringe comprises the first solution and a second syringe comprises the second solution and wherein the blended solution undergoes covalent crosslinking to gel in from about 1 second to about 10 seconds.
15. The method of 14 wherein the volume of the first solution and the volume of the second solution are equal and wherein the first syringe and the second syringe are connected by a plunger cap, and wherein directing the blended solution into a positioned catheter comprises pressing the plunger cap to deploy equal volumes of the first solution and the second solution.

16. The method of 9 wherein the catheter comprises an egress limiter comprising a tubular member and the cap element fixedly attached to the tubular member at or near the distal end of the tubular member, wherein the egress limiter has an inner diameter larger than the outer diameter of the catheter such that the egress limiter can slide over the catheter and wherein the egress limiter has been positioned to adjust a distal catheter length, wherein a distal catheter length comprises a length from the distal end of the catheter to the distal end of the cap element, the method further comprising inserting the catheter into the uterus until the cap element is positioned against the cervix prior to the directing.

17. The method of 16 further comprising measuring the fundal depth of the uterus with a uterine sound and using the fundal depth measurement to adjust the distal catheter length.

18. The method of 16 further comprising after a selected period of time, removing the catheter while leaving the egress limiter in place to block fluid from exiting the cervix.

19. The method of 18 further comprising after a selected period of time, removing the egress limiter while leaving an in-situ formed hydrogel in the uterine cavity.

20. The method of 9 further comprising monitoring the delivering of the blended solution into a uterus with ultrasound.

21. The method of 12 wherein the formed hydrogel acts as a tamponade of further fluid egress.

22. The method of 12 wherein the hydrogel comprises gas microbubbles, microparticles comprising a therapeutic agent, hydrophobic microdomains, hydrogel particles, suspended inorganic particles, and/or microparticulates of a therapeutic agent.

23. The method of 12 wherein the hydrogel comprises iodine, TIB, 2, 3, 5-triiodobenzoic acid, 3, 4, 5-triiodophenol, erythrosine, rose bengal, 3, 5-Bis(acetylamino)-2, 4, 6-triiodobenzoic acid, and 3, 5-Diacetamido-2, 4, 6-triiodobenzoic acid, barium sulfate, titanium, bismuth chloride, or a combination thereof.

CITED TECHNICAL ARTICLES
(INCORPORATED HEREIN BY REFERENCE TO THE EXTENT INDICATED BELOW)

1. Di Spiezio Sardo, A., Calagna, G., Scognamiglio, M., O'Donovan, P., Campo, R., & De Wilde, R. L. (2016). Prevention of intrauterine post-surgical adhesions in hysteroscopy. A systematic review. *European Journal of Obstetrics and Gynecology and Reproductive Biology*, 203, 182-192. doi.org/10.1016/j.ejogrb.2016.05.050.
2. Hesham Al-Inany. Intrauterine adhesions. An update. *Acta Obstet Gynecol Scand* 2001; 80: 986-993.
3. Schenker, J. G. (1996). Etiology of and therapeutic approach to synechia uteri. *European Journal of Obstetrics and Gynecology and Reproductive Biology*, 65(1), 109-113. doi.org/10.1016/0028-2243(95)02315-J.
4. Gomel, V. et al.: Pathophysiology of Adhesion Formation and Strategies for Prevention. J. Repro. Med. 41:1, 1996
5. Acunzo, G., et al. (2003). Effectiveness of auto-crosslinked hyaluronic acid gel in the prevention of intrauterine adhesions after hysteroscopic adhesiolysis: A prospective, randomized, controlled study. *Human Reproduction*, 18(9), 1918-1921. doi.org/10.1093/humrep/deg368.
6. Guida, M., et al. (2004). Effectiveness of auto-crosslinked hyaluronic acid gel in the prevention of intrauterine adhesions after hysteroscopic surgery: A prospective, randomized, controlled study. *Human Reproduction*, 19(6), 1461-1464. doi.org/10.1093/humrep/deh238.
7. Johns D A, et al., Initial feasibility study of a sprayable hydrogel adhesion barrier system in patients undergoing laparoscopic ovarian surgery. *J Am Assoc Gynecol Laparosc* 10 (3):334-338, 2003.
8. Taskin, O., et al., (2000). Role of endometrial suppression on the frequency of intrauterine adhesions after resectoscopic surgery. *Journal of the American Association of Gynecologic Laparoscopists*, 7(3), 351-354. doi.org/10.1016/S1074-3804(05) 60478-1. Ectopic Pregnancy, Endometriosis, Adhesiolysis, and Myomectomy. Curr. Opin. Obstet.
9. diZerega, G. S.: Use of Adhesion Prevention Barriers in Ovarian Surgery, Tubalplasty, Ectopic Pregnancy, Endometriosis, Adhesiolysis, and Myomectomy. Curr. Opin. Obstet. Gynechol. 8:3, 1996.
10. Drug Facts and Comparisons. Facts and Comparisons, Publishers, St. Louis MO 1996.
11. Taskin, O., Sadik, S., Onoglu, A., Gokdeniz, R., Erturan, E., Burak, F., & Wheeler, J. M. (2000). Role of endometrial suppression on the frequency of intrauterine adhesions after resectoscopic surgery. *Journal of the American Association of Gynecologic Laparoscopists*, 7(3), 351-354. doi.org/10.1016/S1074-3804(05)60478-1.
12. Al-Inany, H. (2001). Intrauterine adhesions: An update. *Acta Obstetricia et Gynecologica Scandinavica*, 80(11), 986-993. doi.org/10.1034/j.1600-0412.2001.801103.x.
13. Diamond, M. P., Daniell, J. F., Feste, J., Surrey, M. W., McLaughlin, D. S., Friedman, S., Vaughn, W. K., Martin, D. C. (1987). Adhesion reformation and de novo adhesion formation after reproductive pelvic surgery. *Fertility and Sterility*, 47(5), 864-866. doi.org/10.1016/S0015-0282 (16)59181-X.
14. Raziel A., Arieli Sholmo: Investigation of the uterine cavity in recurrent aborters. *Fertil Steril* 1994; 62: 5, 1080-1082.
15. Schenker, J. G., & Margalioth, E. J. (1982). Intrauterine adhesions: an updated appraisal. *Fertility and Sterility*, 37(5), 593-610. doi.org/10.1016/s0015-0282(16)46268-0.
15. March C M. Update: Intrauterine adhesions. Fertil News 1996; Vol. XVIV, No. 1. Forum
16. Taylor, P. J., Cumming, D. C., & Hill, P. J. (1981). Significance of intrauterine adhesions detected hysteroscopically in eumenorrheic infertile women and role of antecedent curettage in their formation. *American Journal of Obstetrics and Gynecology*, 139(3), 239-242. doi.org/10.1016/0002-9378(81)90001-6.
17. Nappi, C., Di Spiezio Sardo, A., Greco, E., Guida, M., Bettocchi, S., & Bifulco, G. (2007). Prevention of adhesions in gynaecological endoscopy. *Human Reproduction Update*, 13(4), 379-394. doi.org/10.1093/humupd/dm1061.
18. Nappi, C., Di Spiezio Sardo, A., Greco, E., Guida, M., Bettocchi, S., & Bifulco, G. (2007). Prevention of adhesions in gynaecological endoscopy. *Human Reproduction Update*, 13(4), 379-394. doi.org/10.1093/humupd/dm1061.
19. Piredda, A., Marconi, D., Exacoustos, C., Sorrenti, G., Zumpano, A., Szabolcs, B., . . . Zupi, E. (2003). Initial Feasibility Study of an Hydrogel Adhesion Barrier System in Patients Treated by Operative Hysteroscopy for Intrauterine Benign Pathologies. 32° *Annual Meeting of the AAGL*, Las Vegas, Novembre 19-22, 2003, 10(3), 25-26.

20. Victory, R., Berman, J., Diamond, M., Kruger, M., & Mcneeley, S. (2004). Evaluate the Safety and Efficacy of FlowFil Preventing Postoperative Uterine Bleeding and ThermaChoice Endometrial Ablation: 33° *Annual Meeting of the AAGL*, San Francisco, Novembre 10-13, 2004, 11(3), 29-30.

The embodiments above are intended to be illustrative and not limiting. Additional embodiments are within the claims. In addition, although the present invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein. To the extent that specific structures, compositions and/or processes are described herein with components, elements, ingredients or other partitions, it is to be understood that the disclosure herein covers the specific embodiments, embodiments comprising the specific components, elements, ingredients, other partitions or combinations thereof as well as embodiments consisting essentially of such specific components, ingredients or other partitions or combinations thereof that can include additional features that do not change the fundamental nature of the subject matter, as suggested in the discussion, unless otherwise specifically indicated.

What is claimed is:

1. A medical hydrogel system comprising:
   a precursor blend solution comprising an aqueous solvent, a first precursor having a hydrophilic core and succinimidyl ester functional groups, and a second precursor having a plurality of amine functional groups, wherein the precursor blend solution has an acid pH and is stable for at least about five minutes; and
   an accelerator solution comprising a buffer solution having a pH from greater than 8.2 to 12, wherein a mixture of the precursor blend solution and the accelerator solution has a pH of more than 8 and a weight percent solids from about 3% to about 20% and forms a product hydrogel.

2. The medical hydrogel system of claim 1 wherein the hydrophilic core comprises a polyether, a co-polymer of a polyether, a poloxamer, polyvinyl alcohol, poly (vinyl pyrrolidinone), a poly (amino acid), a polysaccharide, or a protein.

3. The medical hydrogel system of claim 1 wherein the hydrophilic core comprises polyethylene glycol.

4. The medical hydrogel system of claim 1 wherein the hydrophilic core comprises a poloxamer or hyaluronic acid.

5. The medical hydrogel system of claim 1 wherein the first precursor comprises a multi-armed polyethylene glycol.

6. The medical hydrogel system of claim 5 wherein the multi-armed polyethylene glycol has from 4 to 8 arms.

7. The medical hydrogel system of claim 1 wherein the first precursor has a molecular weight from about 5 kDa to about 40 kDa.

8. The medical hydrogel system of claim 1 wherein the succinimidyl ester function group comprises N-hydroxy succinimidyl succinate (SS), N-hydroxy sulfosuccinimidyl succinate, N-hydroxy sulfosuccinimidyl gluterate, succinimidyl glutarate (SG), or a mixture thereof.

9. The medical hydrogel system of claim 1 wherein the first precursor comprises a polyethyelene glycol having a molecular weight of from about 10 KDa to about 25 KDa and from 4 to 8 arms, wherein the arms are terminated by N-hydroxy succinimidyl succinate (SS) or succinimidyl glutarate (SG) functional groups.

10. The medical hydrogel system of claim 1 wherein the second precursor comprises lysine, dilysine, trilysine, tetralysine, pentalysine, polyethylenimines, or an amine-terminated polyethylene glycol.

11. The medical hydrogel system of claim 1 wherein the precursor blend solution comprises a molar ratio of the succinimidyl ester functional groups to the amine functional groups from about 2 to about 0.5.

12. The medical hydrogel system of claim 11 wherein the weight percent solids is from about 6% to about 20%.

13. The medical hydrogel system of claim 1 wherein the precursor blend solution comprises a molar ratio of the succinimidyl ester functional groups to the amine functional groups of about 1.

14. The medical hydrogel system of claim 1 wherein the weight percent solids is from about 7.5% to about 15%.

15. The medical hydrogel system of claim 1 wherein the acid pH is in the range of about 4 to about 5.5 and is buffered.

16. The medical hydrogel system of claim 1 wherein the solvent comprises an acidic biological buffer having a concentration from about 0.002M to about 0.15 M.

17. The medical hydrogel system of claim 16 wherein the acidic biological buffer comprises a sodium phosphate monobasic buffer having a pH from about 4 to about 5.5 and wherein the precursor blend solution is stable for 10 minutes to 10 hours.

18. The medical hydrogel system of claim 1 wherein the accelerator solution has a pH in the range of about 8.5 to 10.0.

19. The medical hydrogel system of claim 18 wherein the accelerator solution comprises one or more biological buffer comprising a borate, a phosphate, a citrate, a bicarbonate, CHES, TAPS, Bicine, Tris, or Tricine.

20. The medical hydrogel system of claim 1 wherein the accelerator solution has a buffer concentration from about 0.05 M to about 1.0 M.

21. The medical hydrogel system of claim 1 further comprising an ultrasound contrast agent.

22. The medical hydrogel system of claim 1 further comprising a radiopaque agent.

23. The medical hydrogel system of claim 1 wherein the aqueous solvent comprises an acidic biological buffer, the first precursor comprises a polyethylene glycol having a molecular weight from about 10 kDa to about 50 kDa, 4-8 arms and succinimidyl glutarate (SG) and/or N-hydroxy succinimidyl succinate (SS) functional groups, the second precursor comprises trilysine acetate or a polyethylene glycol having a molecular weight from about 10 kDa to about 25 kDa, 6-8 arms and primary amine functional groups, wherein the precursor blend solution has a pH from about 3.8 to about 4.2 and a molar ratio of the SG functional groups to the primary amine functional groups of about 1, wherein the accelerator solution comprises a biological buffer and has a pH from about 9.6 to about 10.1, wherein the mixture has a weight percent solids of about 3.5% to about 15% and wherein the mixture further comprises a visualization agent.

24. The medical hydrogel system of claim 23 wherein the visualization agent comprises solid particulates comprising barium sulfate, titanium, bismuth chloride, or a combination thereof.

25. The medical hydrogel system of claim 1 wherein the aqueous solvent comprises an acidic biological buffer, the first precursor comprises a polyethylene glycol having a molecular weight from about 30 kDa to about 50 kDa, 4-6 arms and succinimidyl glutarate (SG) functional groups, the second precursor comprises a polyethylene glycol having a molecular weight from about 10 kDa to about 25 kDa, 6-8 arms and primary amine functional groups, wherein the precursor blend solution has a pH from about 3.8 to about 4.2 and a molar ratio of the SG functional groups to the primary amine functional groups of about 1, and wherein the accelerator solution comprises a biological buffer and has a pH from about 9.6 to about 10.1.

26. The medical hydrogel system of claim 1 wherein the aqueous solvent comprises an acidic biological buffer, the first precursor comprises a polyethylene glycol having a molecular weight from about 10K to about 25K, 6-8 arms and succinimidyl glutarate (SG) functional groups, the second precursor comprises trilysine acetate, wherein the precursor blend solution has a pH from about 3.8 to about 4.2 and a molar ratio of the SG functional groups to the amine functional groups of about 1, and wherein the accelerator solution comprises a biological buffer and has a pH from about 9.6 to about 10.1.

27. The medical hydrogel system of claim 1 wherein the aqueous solvent comprises an acidic biological buffer, the first precursor comprises a polyethylene glycol having a molecular weight from about 15K to about 30K, 4-6 arms and succinimidyl glutarate (SG) functional groups, the second precursor comprises trilysine acetate, wherein the precursor blend solution has a pH from about 3.8 to about 4.2 and a molar ratio of the SG functional groups to the amine functional groups of about 1, and wherein the accelerator solution comprises a biological buffer and has a pH from about 9.6 to about 10.1.

28. The medical hydrogel system of claim 1 wherein the aqueous solvent comprises an acidic biological buffer, the first precursor comprises a polyethylene glycol having a molecular weight from about 10K to about 25K, 6-8 arms and N-hydroxy succinimidyl succinate (SS) functional groups, the second precursor comprises trilysine acetate, wherein the precursor blend solution has a pH from about 3.8 to about 4.2 and a molar ratio of the SS functional groups to the amine functional groups of about 1, and wherein the accelerator solution comprises a biological buffer and has a pH from about 9.6 to about 10.1.

29. A method for preventing formation of adhesions within a body cavity comprising:
combining the precursor blend solution and the accelerator solution of claim 1 to form the mixture and
directing the mixture into a catheter to deliver the mixture into a body cavity, wherein the mixture undergoes covalent crosslinking to gel in no more than about 30 seconds.

30. The medical hydrogel system of claim 1 wherein the mixture gels in from about 1 second to about 10 seconds.

31. The medical hydrogel system of claim 1 wherein the mixture gels in situ in no more than about 15 seconds and forms a product hydrogel that has an initial Young's modulus, evaluated 12 hours after initial gelling, from about 10 kPa to about 300 kPa.

32. The medical hydrogel system of claim 1 wherein the product hydrogel substantially fills a body cavity.

33. The medical hydrogel system of claim 32 wherein the body cavity is a uterus.

34. The medical hydrogel system of claim 1 wherein in a time of up to 24 hours after forming, the product hydrogel swells by no more than 125%.

35. The medical hydrogel system of claim 1 wherein the product hydrogel after 14 days in a uterine environment has a Young's modulus that is greater than about 10% of the initial Young's modulus.

36. The medical hydrogel system of claim 1 wherein the product hydrogel persists in a uterine environment for 3 to 29 days.

* * * * *

UNITED STATES PATENT AND TRADEMARK OFFICE
CERTIFICATE OF CORRECTION

PATENT NO. : 12,343,454 B2
APPLICATION NO. : 17/522727
DATED : July 1, 2025
INVENTOR(S) : Bassett et al.

Page 1 of 1

It is certified that error appears in the above-identified patent and that said Letters Patent is hereby corrected as shown below:

On the Title Page

On Page 2, Column 2, Item (56), under "OTHER PUBLICATIONS", Line 18, delete "Gynelogical" and insert -- Gynecological --, therefor.

In the Claims

In Column 49, Claim 9, Line 63, delete "polyethyelene" and insert -- polyethylene --, therefor.

In Column 49, Claim 9, Line 64, delete "10 KDa to about 25 KDa" and insert -- 10 kDa to about 25 kDa --, therefor.

Signed and Sealed this
Second Day of September, 2025

Coke Morgan Stewart
*Acting Director of the United States Patent and Trademark Office*